(12) United States Patent
Tisdale et al.

(10) Patent No.: US 8,207,310 B2
(45) Date of Patent: Jun. 26, 2012

(54) ANTIBODIES TO PROTEOLYSIS INDUCING FACTOR (PIF) RECEPTOR AND METHODS OF USE THEREOF

(75) Inventors: Michael John Tisdale, Claverdon (GB); Penio Todorov, Abingdon (GB); Stacey Marie Wyke, Cardiff (GB)

(73) Assignee: Ashton University, Birmingham (GB)

( * ) Notice: Subject to any disclaimer, the term of this patent is extended or adjusted under 35 U.S.C. 154(b) by 0 days.

(21) Appl. No.: 12/518,881

(22) PCT Filed: Dec. 11, 2007

(86) PCT No.: PCT/GB2007/004726
§ 371 (c)(1),
(2), (4) Date: Dec. 14, 2009

(87) PCT Pub. No.: WO2008/071934
PCT Pub. Date: Jun. 19, 2008

(65) Prior Publication Data
US 2010/0111974 A1    May 6, 2010

(30) Foreign Application Priority Data
Dec. 11, 2006  (GB) .................................. 0624687.0

(51) Int. Cl.
*C12P 21/08*  (2006.01)
*A61K 39/395*  (2006.01)
*A61K 39/00*  (2006.01)
*C07K 16/00*  (2006.01)

(52) U.S. Cl. ................ 530/387.9; 424/130.1; 424/139.1; 424/141.1; 424/143.1; 530/387.1; 530/388.1

(58) Field of Classification Search .................... None
See application file for complete search history.

(56) References Cited

U.S. PATENT DOCUMENTS
5,530,101 A * 6/1996 Queen et al. ............... 530/387.3

FOREIGN PATENT DOCUMENTS
WO    WO 98/11136     3/1998
WO    WO 03/035848 A1 5/2003

OTHER PUBLICATIONS

Watters D, et al. Biochemistry 22:1811-1819, 1983.*
Todorov PT, et al. Br. J. Cancer 80(11)1734-1737, 1999.*
Adams et al., "The DING Protein: An Autocrine Growth-Stimulatory Protein Related to the Human Synovial Stimulatory Protein," Biochimica et Biophysica Acta, 1586:254-264, Elsevier Science B.V. (2002).
Berna et al., "Ring Up the Curtain on DING Proteins," FEBS Letters, 524:6-10, FEBS (2002).
Database UNIPROT, "Synovial Stimulatory Protein," p. 205, XP-002474068, Retrieved from EBI Accession No. UNIPROT: P80697 (1996).
Hain et al., "Biochemical Characterization and Microsequencing of a 205-kDA Synovial Protein Stimulatory for T Cells and Reactive with Rheumatoid Factor Containing Sera," The Journal of Immunology, 1773-1780, The American Association of Immunologists (1996).
Morales et al., "Serendipitous Discovery and X-Ray Structure of a Human Phosphate Binding Apolipoprotein," Structure, 14:601-609, Elsevier Ltd (2006).
O'Leary, "Advanced Course in Pain and Symptom Management," IAPC News, p. 3, Irish Association for Palliative Care (2005).
Riah et al., "Isolation and Microsequencing of a Novel Cotinine Receptor," Cellular and Molecular Neurobiology, 20 (6):653-664, Plenum Publishing Corporation (2000).
Smith and Tisdale, "Signal Transduction Pathways Involved in Proteolysis-Inducing Factor Induced Proteasome Expression in Murine Myotubes," British Journal of Cancer, 89:1783-1788, Cancer Research UK (2003).
Tisdale, "The Ubiquitin-Proteasome Pathway as a Therapeutic Target for Muscle Wasting," The Journal of Supportive Oncology, 3(3)209-217, Elsevier Inc. (2005).
Todorov et al., "Induction of Muscle Protein Degradation and Weight Loss by a Tumor Product," Cancer Research, 56:1256-1261 (1996).
Todorov et al., "Identification and Characterization of a Membrane Receptor for Proteolysis-Inducing Factor on Skeletal Muscle," Cancer Res., 67(23):11419-11427, American Association for Cancer Research (2007).

* cited by examiner

*Primary Examiner* — Robert Landsman
(74) *Attorney, Agent, or Firm* — DLA Piper LLP (US)

(57) ABSTRACT

The invention characterises and provides a receptor for Proteolysis Inducing Factor (PIF) and associated methods and materials employing the same. These have utility, for example, in the provision of treatments for cachexia.

18 Claims, 29 Drawing Sheets

Figure 1:
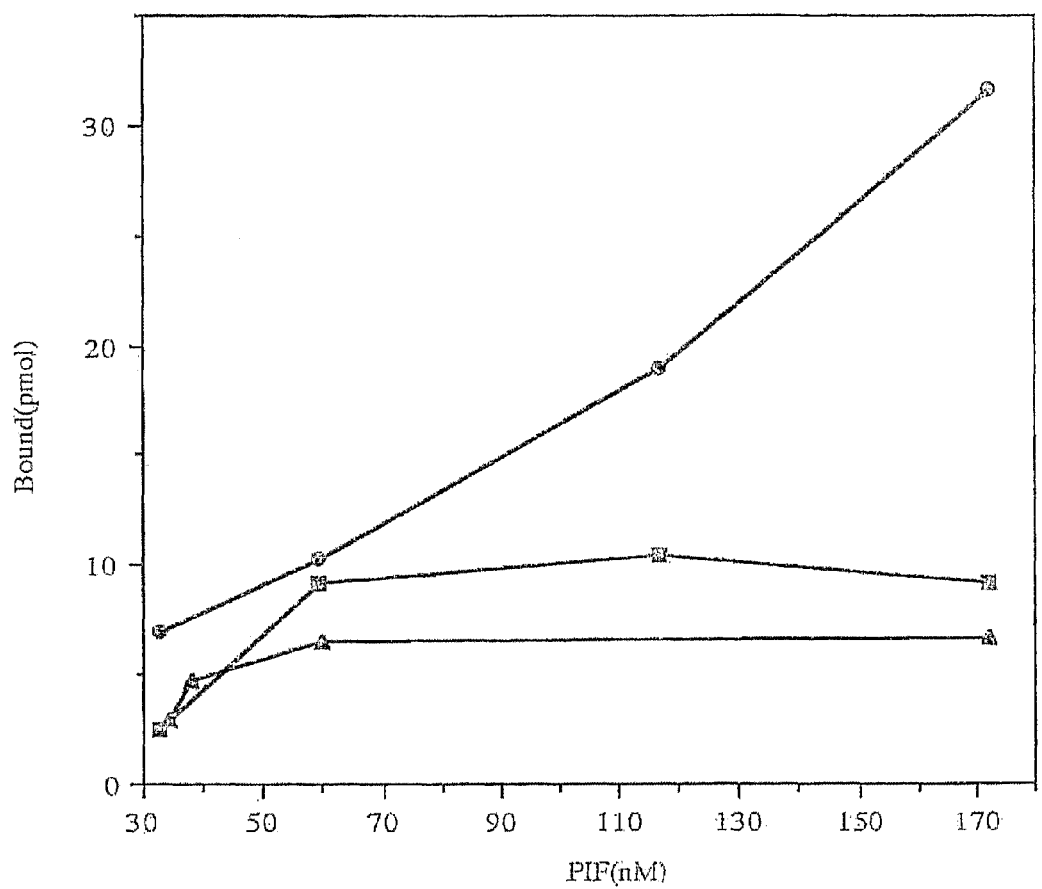

Figure 2
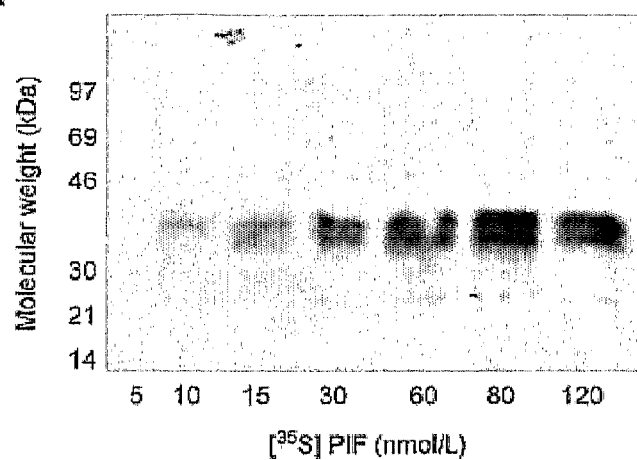
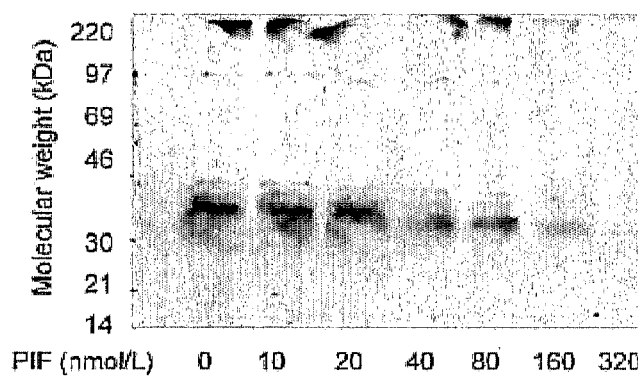
Figure 3
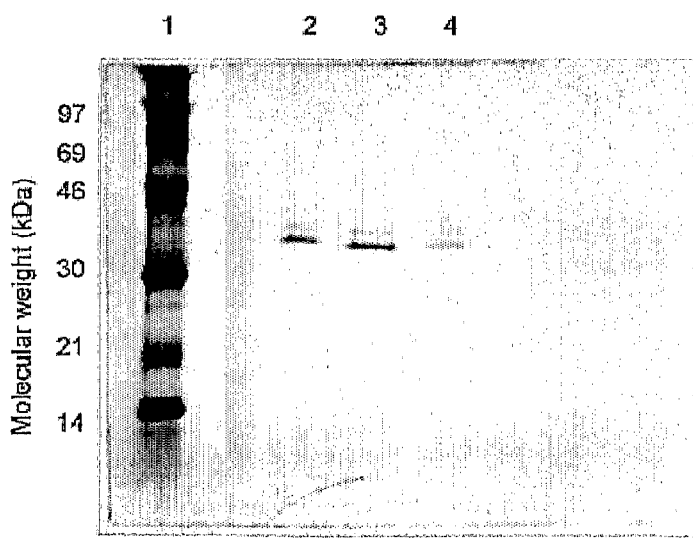

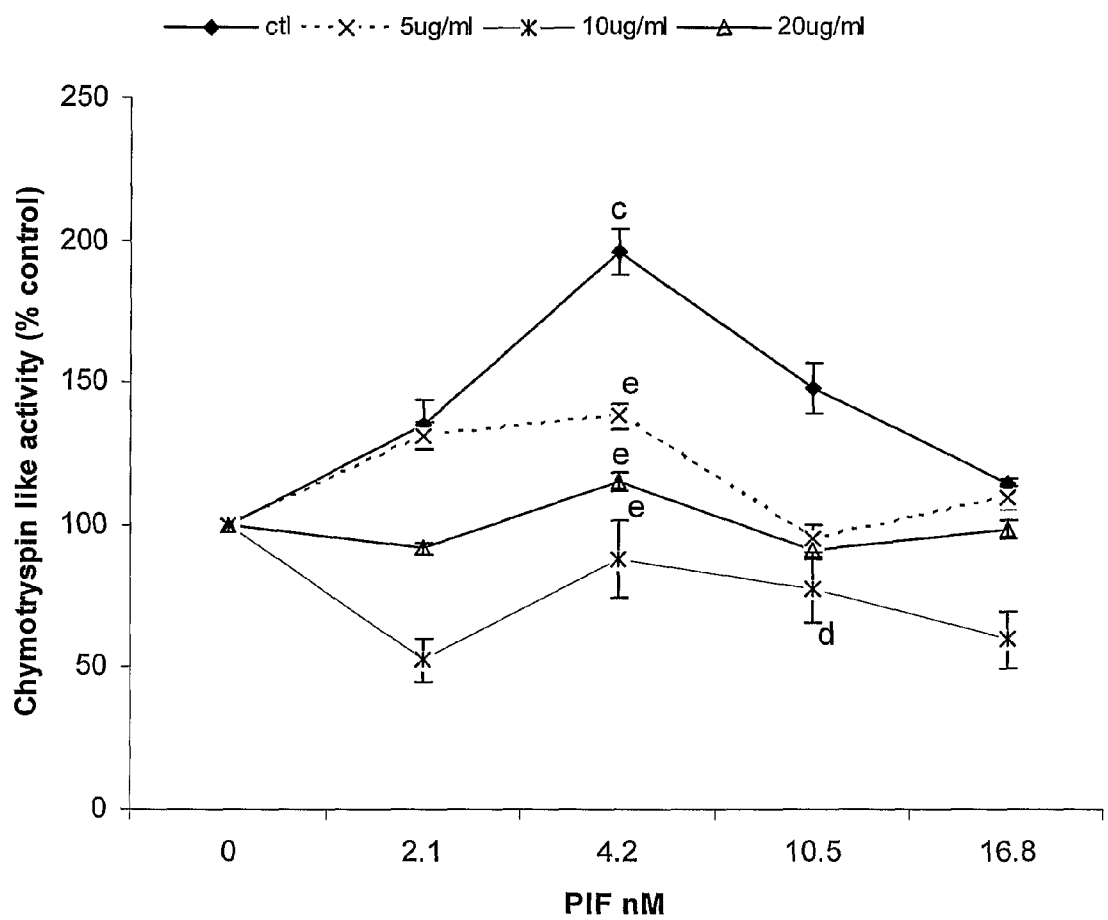

Figure 10A
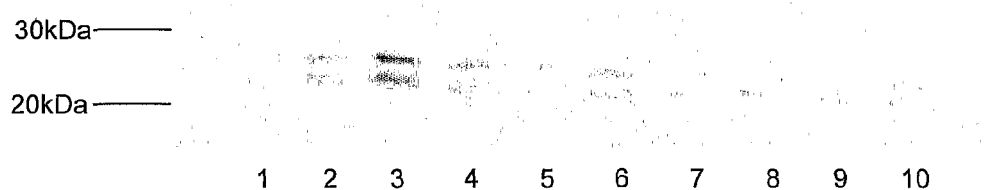
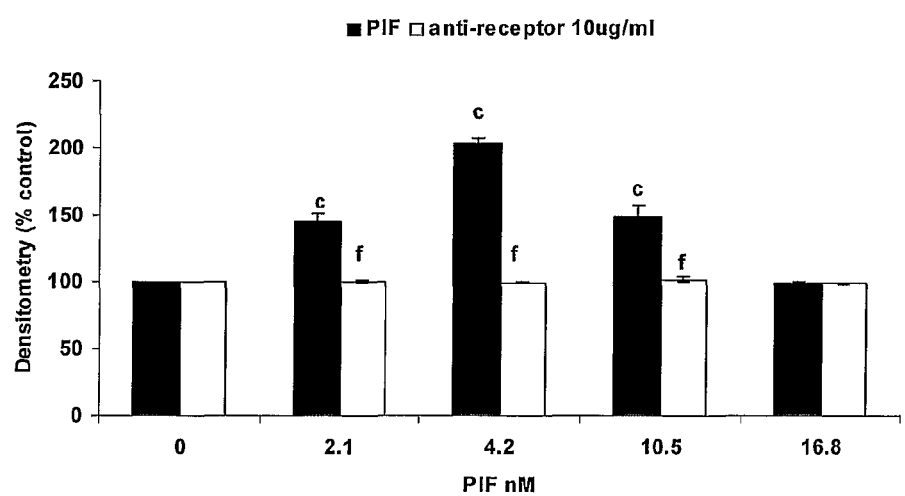

Figure 13A
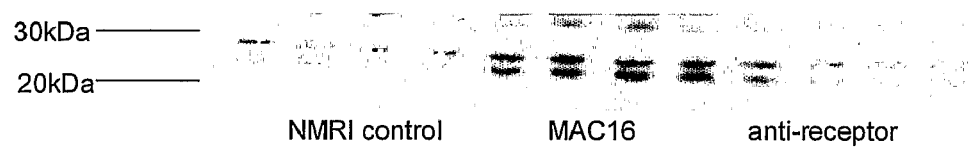
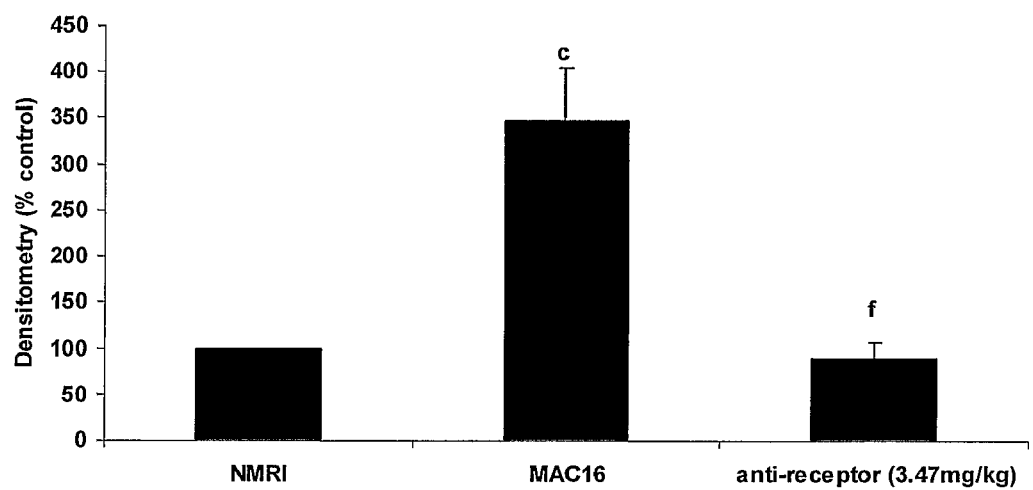

Figure 13E
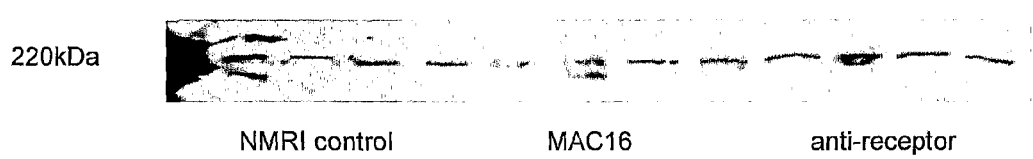
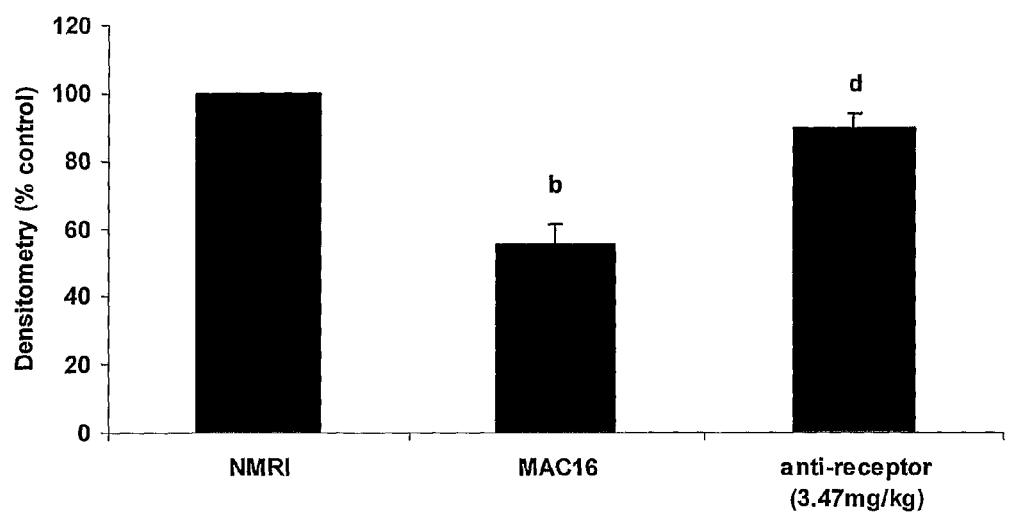

ANTIBODIES TO PROTEOLYSIS INDUCING FACTOR (PIF) RECEPTOR AND METHODS OF USE THEREOF

CROSS REFERENCE TO RELATED APPLICATIONS

This application is a 35 USC §371 National Stage application of International Application No. PCT/GB2007/004726 filed Dec. 11, 2007, now pending; which claims the benefit under 35 USC §119(a) to Great Britain Patent Application No. 0624687.0 filed Dec. 11, 2006. The disclosure of each of the prior applications is considered part of and is incorporated by reference in the disclosure of this application.

The present invention relates to the treatment of cachexia.

Many patients (about 50%) with cancer suffer a severe depletion of their lean body mass as well as adipose tissue, which has been linked with a reduced survival time. Death may occur when up to 30% of body weight is lost and such depletion of body mass can account to over 20% of cancer patient deaths. This condition forms part of a complex metabolic syndrome known as cancer cachexia, in which loss of protein from skeletal muscle is evident, but visceral organs such as liver and kidney are relatively unaffected, thus differentiating this condition from that of, simple starvation. Although a number of cytokines including tumor necrosis factor-α (TNF-α), interleukin-6 (IL-6) and ciliary neurotrophic factor (CNTF) have been associated with protein depletion in cachexia, few studies have reported a direct effect on the degradative process.

The inventor has previously isolated, both from a cachexia-inducing murine tumor and from the urine of cancer patients with cachexia, a tumor factor capable of inducing weight loss in normal mice, with specific depletion of the non-fat carcass mass (Todorov, P., Cariuk, P., McDevitt, T., Coles, B., Fearon, K. and Tisdale, M. Characterization of a cancer cachectic factor. Nature, 379: 739-742, 1996). The loss of body protein was accounted for by an increase in protein degradation and a decrease in protein synthesis in skeletal muscle. This material, which they have called proteolysis inducing factor (PIF), is also capable of inducing protein degradation in isolated gastrocnemius muscle. The effect of PIF on organ weights in normal mice was similar to that seen in cachexia, with a decrease in the weight of soleus and gastrocnemius muscles, no change in the weight of the heart or kidney and an increase in the weight of the liver.

PIF is a sulphated glycoprotein of Mr 24,000 containing both N- and O-linked oligosaccharide chains, which have been shown to be essential for the biological activity (Todorov, P. T., Deacon, M. and Tisdale, M. J. Structural analysis of a tumor-produced sulfated glycoprotein capable of initiating muscle protein degradation. J. Biol. Chem., 272: 12279-12288, 1997). Both mouse and human PIF appear to contain identical carbohydrate components, as defined by their reactivity with a murine monoclonal antibody directed towards the oligosaccharide residues. In addition amino acid sequence analysis of the N-terminal residues showed homology between the two species (Cariuk, P., Lorite, M. J., Todorov, P. T., Field, W. N., Wigmore, S. J. and Tisdale, M. J. Induction of cachexia in mice by a product isolated from the urine of cachectic cancer patients. Br. J. Cancer, 76: 606-613, 1997), suggesting that protein degradation in cancer cachexia may be identical in mouse and man.

In order for PIF to exert a catabolic effect on skeletal muscle the inventors believe that there must be specific cell surface receptors capable of relaying a biological response to the intracellular protein degradative machinery.

It is an object of the present invention to provide a high affinity receptor for PIF; provide agents that are effective for modulating cachexia by interacting with such receptors; and also provide a screen for identifying such agents.

According to a first aspect of the present invention there is provided an isolated receptor for Proteolysis Inducing Factor (PIF) characterised in that the N terminus of the mature native receptor has the amino acid sequence:

| | |
|---|---|
| n-DINGGGATLPQPLYQTAAVLTAGFA. | (SEQ ID No. 1) |
| or: | |
| n-DINGGGATLPQKLYLIPNVL. | (SEQ ID No. 13) | and functional derivatives of either.

The present invention is based upon research conducted by the inventors investigating the binding activity of PIF. These experiments are described in more detail in the accompanying Examples. In brief, the inventors have isolated the receptor from solubilized (1% Triton) membranes of murine myotubules by incubation with radiolabelled PIF. The PIF-receptor complex was purified on a Wheat Germ Agglutinin-Agarose column, which was capable of binding PIF, and the free receptor eluted with 0.1M N-acetylglucosamine. The receptor was found to be a single protein of approximately. Mr 40,000 using 15% SDS-PAGE and Sephadex G-50 exclusion chromatography.

The inventors performed a tryptic digestion followed by sequence analysis (Edman) of the PIF receptor and established that the N-terminus of the mature receptor started with the amino acid sequence of SEQ ID No. 1. This sequence has homology to a peptide fragment from a synovial fluid protein p205, with T-cell stimulatory activity (J. Immunol.; (1996) 157; 1773-80). A further N-terminal sequence was obtained which it is believed may be a polymorphic form (SEQ ID No. 13). This sequence differs by 5 amino acids from SEQ ID No. 1 and is more basic than SEQ ID No. 1. Although not wishing to be bound by mechanism, since PIF is acidic, it is believed that a receptor comprising SEQ ID No. 13 may interact more strongly with it.

Further analysis of the receptor comprising (SEQ ID No. 1 identified internal peptide fragments with the following amino acid sequences:

| | |
|---|---|
| TAINDTFLNADSNLSIGK | (SEQ ID No. 2) |
| XATVAGVSPAPANVSAAIGA | (SEQ ID No. 3) |
| . . . IIPATTAGE . . . | (SEQ ID No. 4) |
| . . . TYMSPDYAAATLAG . . . | (SEQ ID No. 5) |
| FVPLPT | (SEQ ID No. 6) |
| TELSNYVTAXGTxxG | (SEQ ID No. 7) |
| VTTAGSDS | (SEQ ID No. 8) |
| DVNGG | (SEQ ID No. 9) |
| LTTWDLIADSGR | (SEQ ID No. 10) |

The inventors were unable to locate any sequence homology of these internal peptides with other proteins in public databases. Accordingly the PIF receptor according to the present invention represents a novel protein.

It is preferred that the PIF receptor according to the first aspect of the invention further comprises at least one internal peptide sequence of SEQ ID No. 2-10. More preferably the receptor further comprises at least two of such internal peptides and most preferably the receptor comprises each of the internal peptides.

Preferred functional derivatives of the PIF receptor include proteins that may comprise mutations (relative to the wild type) that nevertheless do not alter the activity of the receptor. In accordance with the present invention, preferred further changes in the receptor are commonly known as "conservative" or "safe" substitutions. Conservative amino acid substitutions are those with amino acids having sufficiently similar chemical properties, in order to preserve the structure and the biological function of the receptor. It is clear that insertions and deletions of amino acids may also be made in the above defined sequences without altering their function, particularly if the insertions or deletions only involve a few amino acids, e.g. under ten and preferably under five, and do not remove or displace amino acids which are critical to the functional confirmation of the receptor. The literature provide many models on which the selection of conservative amino acids substitutions can be performed on the basis of statistical and physico-chemical studies on the sequence and/or the structure of a natural protein.

According to second aspect of the present invention there is provided a nucleic acid encoding the receptor according to the first aspect of the invention.

The nucleic acid may be a DNA molecule or RNA molecule (e.g. mRNA). Preferably, the nucleic acid has a nucleotide sequence substantially as set out as SEQ ID No. 11 (predicted sequence for the human N-terminal fragment SEQ ID No. 1 based on the most common codon usage) or a derivative or functional variant thereof.

```
D   I   N   G   G   G   A   T       (SEQ ID NO. 1)
GAC ATC AAC GGC GGC GGC GCC ACC     (SEQ ID NO. 11)

L   P   Q   P   L   Y   Q   T
CTG CCC CAG CCC CTG TAC CAG ACC

A   A   V   L   T   A   G   F
GCC GCC GTG CTG ACC GCC GGC TTC

A
GCC
```

Alternatively, the nucleic acid has a nucleotide sequence substantially as set out as SEQ ID No. 14 (predicted sequence for the human N-terminal fragment SEQ ID No. 13) based on the most common codon usage) or a derivative or functional variant thereof.

```
D   I   N   G   G   G   A   T       (SEQ ID NO. 13)
GAC ATC AAC GGC GGC GGC GCC ACC     (SEQ ID NO. 14)

L   P   Q   K   L   Y   L   I
CTG CCC CAG AAG CTG TAC CTG ATC

P   N   V   L
CCC AAC GTG CTG
```

The nucleic acid may be contained within a suitable vector to form a recombinant vector. Hence, according to a third aspect of the invention there is provided a vector comprising a nucleic acid according to the second aspect. The vector may for example be a plasmid, cosmid or phage. Such recombinant vectors are highly useful for transforming cells with the DNA molecule, for producing the receptor according to the first aspect of the invention.

Recombinant vectors may also include other functional elements. For instance, recombinant vectors can be designed such that the vector will autonomously replicate in the cell. In this case, elements which induce DNA replication may be required in the recombinant vector. Alternatively, the recombinant vector may be designed such that the vector and nucleic acid molecule integrates into the genome of a cell. In this case DNA sequences which favour targeted integration (e.g. by homologous recombination) are desirable. Recombinant vectors may also have DNA coding for genes that may be used as selectable markers in the cloning process. The recombinant vector may also further comprise a promoter or regulator to control expression of the nucleic acid as required.

It will be appreciated by the skilled technician that functional derivatives of the amino acid, and nucleic acid sequences, disclosed herein, may have a sequence which has at least 30%, preferably 40%, more preferably 50%, and even more preferably, 60% sequence identity with the amino acid/polypeptide/nucleic acid sequences of any of the sequences referred to herein. An amino acid/polypeptide/nucleic acid sequence with a greater identity than preferably 65%, more preferably 75%, even more preferably 85%, and even more preferably 90% to any of the sequences referred to is also envisaged. Preferably, the amino acid/polypeptide/nucleic acid sequence has 92% identity, even more preferably 95% identity, even more preferably 97% identity, even more preferably 98% identity and, most preferably, 99% identity with any of the referred to sequences.

Calculation of percentage identities between different amino acid/polypeptide/nucleic acid sequences may be carried out as follows. A multiple alignment is first generated by the ClustalX program (pair wise parameters: gap opening 10.0, gap extension 0.1, protein matrix Gonnet 250, DNA matrix IUB; multiple parameters: gap opening 10.0, gap extension 0.2, delay divergent sequences 30%, DNA transition weight 0.5, negative matrix off, protein matrix gonnet series, DNA weight IUB; Protein gap parameters, residue-specific penalties on, hydrophilic penalties on, hydrophilic residues GPSNDQERK, gap separation distance 4, end gap separation off). The percentage identity is then calculated from the multiple alignment as (N/T)*100, where N is the number of positions at which the two sequences share an identical residue, and T is the total number of positions compared. Alternatively, percentage identity can be calculated as (N/S)*100 where S is the length of the shorter sequence being compared. The amino acid/polypeptide/nucleic acid sequences may be synthesised de novo, or may be native amino acid/polypeptide/nucleic acid sequence, or a derivative thereof.

Alternatively, a substantially similar nucleotide sequence will be encoded by a sequence which hybridizes to any of the nucleic acid sequences referred to herein or their complements under stringent conditions. By stringent conditions, we mean the nucleotide hybridises to filter-bound DNA or RNA in 6× sodium chloride/sodium citrate (SSC) at approximately 45° C. followed by at least one wash in 0.2×SSC/0.1% SDS at approximately 5-65° C. Alternatively, a substantially similar polypeptide may differ by at least 1, but less than 5, 10, 20, 50 or 100 amino acids from the peptide sequences according to the present invention.

Due to the degeneracy of the genetic code, it is clear that any nucleic acid sequence could be varied or changed without substantially affecting the sequence of the receptor protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid.

The accurate alignment of protein or DNA sequences is a complex process, which has been investigated in detail by a number of researchers. Of particular importance is the trade-off between optimal matching of sequences and the introduction of gaps to obtain such a match. In the case of proteins, the means by which matches are scored is also of significance. The family of PAM matrices (e.g., Dayhoff, M. et al., 1978, Atlas of protein sequence and structure, Natl. Biomed. Res. Found.) and BLOSUM matrices quantify the nature and likelihood of conservative substitutions and are used in multiple alignment algorithms, although other, equally applicable matrices will be known to those skilled in the art. The popular multiple alignment program ClustalW, and its windows version ClustalX (Thompson et al., 1994, Nucleic Acids Research, 22, 4673-4680; Thompson et al., 1997, Nucleic Acids Research, 24, 4876-4882) are efficient ways to generate multiple alignments of proteins and DNA.

Frequently, automatically generated alignments require manual alignment, exploiting the trained user's knowledge of the protein family being studied, e.g., biological knowledge of key conserved sites. One such alignment editor programs is Align (at http, on the world wide web, at URL "gwdg.de/~dhepper/download/"; Hepperle, D., 2001: Multicolor Sequence Alignment Editor. Institute of Freshwater Ecology and Inland Fisheries, 16775 Stechlin, Germany), although others, such as JalView or Cinema are also suitable.

Calculation of percentage identities between proteins occurs during the generation of multiple alignments by Clustal. However, these values need to be recalculated if the alignment has been manually improved, or for the deliberate comparison of two sequences. Programs that calculate this value for pairs of protein sequences within an alignment include PROTDIST within the PHYLIP phylogeny package (Felsenstein; at http "evolution.gs.washington.edu/phylip.html") using the "Similarity Table" option as the model for amino acid substitution (P). For DNA/RNA, an identical option exists within the DNADIST program of PHYLIP.

Other modifications in protein sequences are also envisaged and within the scope of the claimed invention, i.e. those which occur during or after translation, e.g. by acetylation, amidation, carboxylation, phosphorylation, proteolytic cleavage or linkage to a ligand.

It will be appreciated that knowledge of the receptor according to the first aspect of the invention enabled the inventors to develop agents that modulate the activity of the receptor and thereby clinically manage cachexia. The present invention also provides a medical use for such agents. Thus, according to a fourth aspect of the invention, there is provided an agent that decreases the biological activity of the PIF receptor according to the first aspect of the invention for use as a medicament.

According to a fifth aspect of the invention there is provided the use of an agent that decreases the biological activity of the PIF receptor in the manufacture of a medicament for the treatment of cachexia.

According to a sixth aspect of the present invention, there is provided a method for the treatment of cachexia comprising administering to a subject in need of such treatment a therapeutically effective amount of an agent that decreases the biological activity of the PIF receptor.

Agents capable of decreasing the biological activity of PIF may achieve their effect by a number of means. For instance, such agents may:

(a) decrease the expression of the PIF receptor;
(b) increase receptor desensitisation or receptor breakdown;
(c) reduce interaction between PIF and its endogenous receptor;
(d) reduces PIF receptor mediated intracellular signalling;
(e) competes with endogenous PIF receptors for PIF binding;
(f) binds to the PIF receptor to block PIF binding; or
(g) binds to PIF preventing interaction with the receptor.

It is preferred that the agent directly interacts with the receptor of PIF (i.e. (e) and (f) above) or it acts to inhibit transcription or translation of the PIF receptor (a) above. It will be appreciated that such agents may only be designed in the light of knowledge of the sequence of the PIF receptor according to the first aspect of the invention.

A preferred agent for use according to the fourth, fifth or sixth aspects of the present invention is a neutralising antibody raised against the PIF receptor. Such antibodies represent an important feature of the invention. Thus, according to a seventh aspect of the invention, there is provided an antibody, or a functional derivative thereof, against the PIF receptor according to the first aspect of the invention.

The antibody preferably blocks PIF receptor mediated intracellular signalling. This may be by blocking the ligand binding site on the receptor or may dissociate the receptor from its signal transduction pathway by some allosteric means.

Antibodies according to the invention may be produced as polyclonal sera by injecting antigen into animals. Preferred polyclonal antibodies may be raised by inoculating an animal (e.g. a rabbit) with antigen using techniques known to the art. The antigen may be the whole PIF receptor (in glycosylated or non-glycosylated form) or a fragment thereof. Preferred fragments for generating the antibodies are peptides with SEQ ID No. 1-10 or 13. A preferred polyclonal antibody is raised against the peptide of SEQ ID No.1 as described in the Examples. Another preferred polyclonal antibody is raised against the peptide of SEQ ID No. 13.

Alternatively the antibody may be monoclonal and raised in mice. Conventional hybridoma techniques may be used to raise the antibodies. The antigen used to generate monoclonal antibodies according to the present invention may be the whole PIF receptor (in glycosylated or non-glycosylated form) or a fragment thereof.

Preferred fragments for generating the antibodies are peptides with SEQ ID No. 1-10 or 13.

It is preferred that the antibody is a γ-immunoglobulin (IgG).

It will be appreciated that the variable region of an antibody defines the specificity of the antibody and as such this region should be conserved in functional derivatives of the antibody according to the invention. The regions beyond the variable domains (C-domains) are relatively constant in sequence. It will be appreciated that the characterising feature of antibodies according to the invention is the $V_H$ and $V_L$ domains. It will be further appreciated that the precise nature of the $C_H$ and $C_L$ domains is not, on the whole, critical to the invention. In fact preferred antibodies according to the invention may have very different $C_H$ and $C_L$ domains. Furthermore, as discussed more fully below, preferred antibody functional derivatives may comprise the Variable domains without a C-domain (e.g. scFV antibodies).

The inventors have found that antibodies, or functional derivatives thereof, according to the seventh aspect of the invention have surprising efficacy for preventing the development of cachexia in cancer patients.

An antibody derivative may have 75% sequence identity, more preferably 90% sequence identity and most preferably has at least 95% sequence identity to a monoclonal antibody or specific antibody in a polyclonal mix. It will be appreciated that most sequence variation may occur in the framework regions (FRs) whereas the sequence of the CDRs of the antibodies, and functional derivatives thereof, is most conserved.

A number of preferred embodiments of the seventh aspect of the invention relate to molecules with both Variable and Constant domains. However it will be appreciated that antibody fragments (e.g. scFV antibodies) are also encompassed by the invention that comprise essentially the Variable region of an antibody without any Constant region.

Antibodies generated in one species are known to have several serious drawbacks when used to treat a different species. For instance when murine antibodies are used in humans they tend to have a short circulating half-life in serum and are recognised as foreign proteins by the patient being treated. This leads to the development of an unwanted human anti-mouse (or rat) antibody response. This is particularly troublesome when frequent administrations of the antibody is required as it can enhance the clearance thereof, block its therapeutic effect, and induce hypersensitivity reactions. Accordingly preferred antibodies (if of non-human source) for use in human therapy are humanised.

Monoclonal antibodies are generated by the hybridoma technique which usually involves the generation of non-human mAbs. The technique enables rodent monoclonal antibodies with almost any specificity to be produced. Accordingly preferred embodiments of the invention may use such a technique to develop monoclonal antibodies against the PIF receptor. Although such antibodies are useful therapeutically, it will be appreciated that such antibodies are not ideal therapeutic agents in humans (as suggested above). Ideally, human monoclonal antibodies would be the preferred choice for therapeutic applications. However, the generation of human mAbs using conventional cell fusion techniques has not to date been very successful. The problem of humanisation may be at least partly addressed by engineering antibodies that use V region sequences from non-human (e.g. rodent) mAbs and C region (and ideally FRs from V region) sequences from human antibodies. The resulting 'engineered' mAbs are less immunogenic in humans than the rodent mAbs from which they were derived and so are better suited for clinical use.

Humanised antibodies may be chimaeric monoclonal antibodies, in which, using recombinant DNA technology, rodent immunoglobulin constant regions are replaced by the constant regions of human antibodies. The chimaeric H chain and L chain genes may then be cloned into expression vectors containing suitable regulatory elements and induced into mammalian cells in order to produce fully glycosylated antibodies. By choosing an appropriate human H chain C region gene for this process, the biological activity of the antibody may be pre-determined. Such chimaeric antibodies are superior to non-human monoclonal antibodies in that their ability to activate effector functions can be tailored for a specific therapeutic application, and the anti-globulin response they induce is reduced.

Such chimaeric molecules are preferred agents for treating cachexia according to the present invention. RT-PCR may be used to isolate the $V_H$ and $V_L$ genes from preferred mAbs, cloned and used to construct a chimaeric version of the mAb possessing human domains.

Further humanisation of antibodies may involve CDR-grafting or reshaping of antibodies. Such antibodies are produced by transplanting the heavy and light chain CDRs of a rodent mAb (which form the antibody's antigen binding site) into the corresponding framework regions of a human antibody.

A further preferred agent for use according to the fourth, fifth or sixth aspects of the present invention is a soluble PIF receptor or a functional derivative or fragment thereof according to the first aspect of the invention. The PIF receptor is an integral protein of the plasma membrane. The inventors have found that soluble receptors according to the first aspect of the invention may be introduced into a target tissue and will compete for endogenous PIF. PIF binding to the soluble receptor will not exert a physiological effect because the soluble receptor is not linked to an intracellular signalling pathway. Accordingly such agents are effective for reducing PIF receptor mediated cachexia. Peptide fragments of the PIF receptor may also be used as agents according to the invention. The inventors believe that the PIF binding site on the receptor may be in the terminal portion. It is therefore preferred that the agent is an N terminal fragment of the PIF receptor. For instance the agent may be the peptide of SEQ ID NO. 1 (see Example 3) or SEQ ID NO. 13.

Derivatives of peptide agents used according to the invention include derivatives that increase the half-life of the agent in vivo. Examples of derivatives capable of increasing the half-life of polypeptides according to the invention include peptoid derivatives, D-amino acid derivatives and peptide-peptoid hybrids.

Proteins and peptide agents according to the present invention may be subject to degradation by a number of means (such as protease activity at a target site). Such degradation may limit their bioavailability and hence therapeutic utility. There are a number of well-established techniques by which peptide derivatives that have enhanced stability in biological contexts can be designed and produced. Such peptide derivatives may have improved bioavailability as a result of increased resistance to protease-mediated degradation. Preferably, a derivative suitable for use according to the invention is more protease-resistant than the protein or peptide from which it is derived. Protease-resistance of a peptide derivative and the protein or peptide from which it is derived may be evaluated by means of well-known protein degradation assays. The relative values of protease resistance for the peptide derivative and peptide may then be compared.

Peptoid derivatives of proteins and peptides according to the invention may be readily designed from knowledge of the structure of the receptor according to the first aspect of the invention or an agent according to the fourth, fifth or sixth aspect of the invention. Commercially available software may be used to develop peptoid derivatives according to well-established protocols.

Retropeptoids, (in which all amino acids are replaced by peptoid residues in reversed order) are also able to mimic proteins or peptides according to the invention. A retropeptoid is expected to bind in the opposite direction in the ligand-binding groove, as compared to a peptide or peptoid-peptide hybrid containing one peptoid residue. As a result, the side chains of the peptoid residues are able to point in the same direction as the side chains in the original peptide.

A further embodiment of a modified form of peptides or proteins according to the invention comprises D-amino acid forms. In this case, the order of the amino acid residues is reversed. The preparation of peptides using D-amino acids rather than L-amino acids greatly decreases any unwanted breakdown of such derivative by normal metabolic processes, decreasing the amounts of the derivative which needs to be administered, along with the frequency of its administration.

A further preferred agent according to the fourth, fifth or sixth aspects of the invention is an antisense DNA or RNA molecule that will bind to endogenous PIF receptor transcripts. Such antisense molecules reduce PIF receptor expression and thereby reduce PIF mediated activity. Preferred antisense molecules represent the antisense of nucleic acids according to the second aspect of the invention. By way of example, the sequence of an antisense molecule against the receptor would be:

(SEQ ID NO. 12)
5' GGCGAAGCCGGCGGTCAGCACGGCGGCGGTCTGGTACAGGGGCTGGG

GCAGGGTGGCGCCGCCGCCGTTGATGTC . . . 3'

The reverse-complement molecule of SEQ ID NO. 12 acts as antisense to the N-terminal 25 amino acids of SEQ ID NO. 1.

(SEQ ID NO. 15)
5' CAGCACGTTGGGGATCAGGTACAGCTTCTGGGGCAGGGTGGCGCCGC

CGCCGTTGATGTC . . . 3'

The reverse-complement molecule of SEQ ID NO. 15 acts as antisense to the N-terminal 20 amino acids of SEQ ID NO. 13.

siRNA may also be used as an agent according to the invention. siRNA forms part of a gene silencing mechanism, known as RNA interference (RNAi) which results in the sequence-specific destruction of mRNAs and enables a targeted knockout of gene expression. siRNA used in gene silencing may comprise double stranded RNA of 21 nucleotides length, typically with a 2-nucleotide overhang at each 3' end. Alternatively, short hairpin RNAs (shRNAs) using sense and antisense sequences connected by a hairpin loop may be used. Both siRNAs and shRNAs can be either chemically synthesized and introduced into cells for transient RNAi or expressed endogenously from a promoter for long-term inhibition of gene expression. siRNA molecules for use as an agent according to the invention may comprise either double stranded RNA of 10-50 nucleotides. Preferably, siRNAs for use as an agent according to the invention comprise 18-30 nucleotides. More preferably, siRNAs for use as an agent according to the invention comprise 21-25 nucleotides. And most preferably, siRNAs for use as an agent according to the invention comprise 21 nucleotides. It will be appreciated that siRNAs will need to be based upon the sequences according to the second aspect of the invention. Preferred double stranded siRNA molecules comprise a sense strand of 21-25 contiguous nucleotides from SEQ ID NO. 11 bound to the complementary antisense strand (e.g. as defined in SEQ. ID NO. 12). Alternatively, shRNAs using sense and antisense sequences may be used as an agent according to the invention. Preferably, shRNAs using sense and antisense sequences that may be employed as an agent according to the invention comprise 20-100 nucleotides. More preferably, shRNAs using sense and antisense sequences that may be employed as an agent according to the invention comprise 42 nucleotides and may comprise 21 nucleotides from SEQ ID NO. 11 linked to the complementary 21 nucleotides from SEQ ID NO. 12 (or SEQ ID NO. 14 linked to 15). As for siRNAs, it will be appreciated that shRNAs will need to be based upon the sequences according to the second aspect of the invention.

The inventor has realised that PIF binds to its receptor through oligosaccharide chains. Accordingly, other preferred agents have a similar configuration of oligosaccharides to those found on PIF and/or its receptor (e.g. chondroitin sulphate or other sulphoid oligosaccharides) Such agents compete with PIF for binding to the receptor and are therefore useful for reducing cachexia.

Agents according to the fourth, fifth or sixth aspects of the invention may take a number of different forms depending, in particular on the manner in which the composition is to be used. Thus, for example, a composition comprising the agent may be in the form of a powder, tablet, capsule, liquid, ointment, cream, gel, hydrogel, aerosol, spray, micelle, transdermal patch, liposome or any other suitable form that may be administered to a person or animal. It will be appreciated that the vehicle of the composition of the invention should be one which is well tolerated by the subject to whom it is given and enables delivery of the compounds to the brain.

The composition of the invention may be used in a number of ways. For instance, systemic administration may be required in which case the agent may be contained within a composition which may, for example, be ingested orally in the form of a tablet, capsule or liquid. Alternatively the composition may be administered by injection into the blood stream. Injections may be intravenous (bolus or infusion) or subcutaneous (bolus or infusion) or intramuscularly. The agents may be administered by inhalation (e.g. intranasally). The agents may also be administered centrally by means of intracerebral, intracerebroventricular or intrathecal delivery.

The agents may also be incorporated within a slow or delayed release device. Such devices may, for example, be inserted on or under the skin and the agent may be released over weeks or even months. Such a device may be particularly useful for chronically ill patients. The devices may be particularly advantageous when an agent is used which would normally require frequent administration (e.g. at least daily ingestion of a tablet or daily injection).

It will be appreciated that the amount of an agent required is determined by biological activity and bioavailability which in turn depends on the mode of administration, the physicochemical properties of the agent employed and whether it is being used as a monotherapy or in a combined therapy. The frequency of administration will also be influenced by the abovementioned factors and particularly the half-life of the agent within the subject being treated.

Optimal dosages to be administered may be determined by those skilled in the art, and will vary with the particular agent in use, the strength of the preparation, the mode of administration, and the advancement of the disease condition (e.g. the severity of the cachexia or event the stage of cancer development). Additional factors depending on the particular subject being treated will result in a need to adjust dosages, including subject age, weight, gender, diet, and time of administration.

Known procedures, such as those conventionally employed by the pharmaceutical industry (e.g. in vivo experimentation, clinical trials, etc.), may be used to establish specific formulations of compositions and precise therapeutic regimes (such as daily doses of the compounds and the frequency of administration).

Generally, a daily dose of between 0.01 μg/kg of body weight and 1.0 g/kg of body weight of an agent (e.g. a soluble receptor based on SEQ ID NO. 1) may be used for the treatment of cachexia. The amount used will depend upon which specific agent is used. More preferably, the daily dose is between 0.01 mg/kg of body weight and 100 mg/kg of body weight.

Daily doses may be given as a single administration (e.g. a daily tablet for oral consumption or as a single daily injection). Alternatively, the agent used may require administration twice or more times during a day. As an example, an agent may be administered as two (or more depending upon the severity of the cachexia) daily doses of between 25 mgs and 5000 mgs in tablet form. A patient receiving treatment may take a first dose upon waking and then a second dose in the evening (if on a two dose regime) or at 3 or 4 hourly intervals thereafter. Alternatively, a slow release device may be used to provide optimal doses to a patient without the need to administer repeated doses.

The use of an antibody raised against the PIF receptor as an agent according to the invention may involve the administration thereof as a weekly, twice weekly or thrice weekly dose (or more depending upon the severity of the cachexia) of between 25 mgs and 5000 mgs in injectable form. Alternatively, a slow release device may be used to provide optimal doses to a patient without the need to administer repeated doses.

This invention further provides a pharmaceutical composition comprising a therapeutically effective amount of an agent of the invention and a pharmaceutically acceptable vehicle. In one embodiment, the amount of the agent (e.g. a soluble receptor) is an amount from about 0.01 mg to about 800 mg. In another embodiment, the amount is from about 0.01 mg to about 500 mg.

In a further embodiment, the vehicle is a liquid and the composition is a solution. In another embodiment, the vehicle is a solid and the composition is a tablet. In a further embodiment, the vehicle is a gel and the composition is a suppository.

Agents are preferably combined with a pharmaceutically acceptable vehicle prior to administration.

In the subject invention a "therapeutically effective amount" is any amount of an agent which, when administered to a subject suffering from a disease against which the agent is effective, causes reduction, remission, or regression of the cachexia through the preservation of lean body mass. A "subject" is a vertebrate, mammal, domestic animal or preferably a human being.

In the practice of this invention a "pharmaceutically acceptable vehicle" is any physiological vehicle known to those of ordinary skill in the art useful in formulating pharmaceutical compositions.

In one embodiment, the pharmaceutical vehicle may be a liquid and the pharmaceutical composition would be in the form of a solution. In another embodiment, the pharmaceutically acceptable vehicle is a solid and the composition is in the form of a powder or tablet. In a further embodiment, the pharmaceutical vehicle is a gel and the composition is in the form of a suppository or cream. In a further embodiment the agent or composition may be formulated as a part of a pharmaceutically acceptable transdermal patch.

A solid vehicle can include one or more substances which may also act as flavoring agents, lubricants, solubilizers, suspending agents, fillers, glidants, compression aids, binders or tablet-disintegrating agents; it can also be an encapsulating material. In powders, the vehicle is a finely divided solid which is in admixture with the finely divided active ingredient. In tablets, the active ingredient is mixed with a vehicle having the necessary compression properties in suitable proportions and compacted in the shape and size desired. The powders and tablets preferably contain up to 99% of the active ingredient. Suitable solid vehicles include, for example, calcium phosphate, magnesium stearate, talc, sugars, lactose, dextrin, starch, gelatin, cellulose, polyvinylpyrrolidine, low melting waxes and ion exchange resins.

Liquid vehicles are used in preparing solutions, suspensions, emulsions, syrups, elixirs and pressurized compositions. The active ingredient can be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The agents may be prepared as a sterile solid composition which may be dissolved or suspended at the time of administration using sterile water, saline, or other appropriate sterile injectable medium. Vehicles are intended to include necessary and inert binders, suspending agents, lubricants, flavorants, sweeteners, preservatives, dyes, and coatings.

The agents can be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like.

An agent can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The agents may be combined with a pharmaceutically acceptable vehicle and another therapeutically active agent prior to administration. The other therapeutically active agent may be for the treatment of cancer or cachexia.

Knowledge of the PIF receptor has enabled the inventors to develop a screen for identifying whether or not test compounds are putative agents for use according to the fourth, fifth or sixth aspects of the invention. Thus, according to a eighth aspect of the present invention there is provided a method of screening a compound to test whether or not the compound has efficacy for treating cachexia, comprising:

(i) exposing cells or membranes comprising PIF receptors according to the first aspect of the invention to a test compound for a predetermined length of time;

(ii) detecting the activity or expression of the PIF receptor; and (iii) comparing the activity or expression of the PIF receptors in the cells or membranes treated with the compound relative to activity or expression found in control cells or membranes that were not treated with the compound wherein compounds with efficacy for treating cachexia decrease activity or decrease expression of the PIF receptor relative to the controls.

It will be appreciated that the method according to the eighth aspect of the invention may be adapted such that it is used to test whether or not a compound causes cachexia. Therefore according to a ninth aspect of the invention there is provided a method of screening a compound, to test whether or not the compound causes cachexia, comprising:

(i) exposing cells or membranes comprising PIF receptors according to the first aspect of the invention to a test compound for a predetermined length of time;

(ii) detecting the activity or expression of the PIF receptor; and (iii) comparing the activity or expression of the PIF receptors in the cells or membranes treated with the compound relative to activity or expression found in control cells or membranes that were not treated with the compound wherein compounds that cause cachexia increase activity or increase expression of the PIF receptor relative to the controls.

With regards to "detecting the activity or expression of the PIF receptor" according to the eighth and the ninth aspects of the present invention, by "activity" of the PIF receptor we mean the detection of ligand-receptor binding; detection of receptor-mediated intracellular signal transduction; or determination of an end-point physiological effect. By "expression" we mean detection of the receptor protein either in the cell membrane, the Endoplasmatic Reticulum or the Golgi Apparatus; or detection of the mRNA encoding the receptor protein.

The screening methods of the invention are based upon the inventors' realisation that the extent of PIF receptor expression and/or activity may be closely related to the development of cachexia.

Cells used according to the eighth or ninth aspects of the invention may be contained within an experimental animal (e.g. a mouse or rat) when the method is an in vivo based test. Alternatively the cells may be in a tissue sample (for ex vivo based tests) or the cells may be grown in culture. It will be appreciated that such cells should express, or may be induced to express, functional PIF receptor.

It is also possible to use cells that are not naturally predisposed to express PIF receptor provided that such cells are transformed with an expression vector according to the third aspect of the invention. Such cells represent preferred test cells for use according to the invention. This is because animal cells or even prokaryotic cells may be transformed to express human PIF receptor and therefore represent a good cell model for testing the efficacy of candidate drugs for use in human therapy.

The methods according to the eighth and ninth aspects of the invention may also be based upon the use of cell membranes comprising the PIF receptor or the isolated soluble PIF receptor. Such membranes are preferably derived from the above described cells. Such membranes may not comprise functional PIF receptors but may be prepared such that the membranes may be used in receptor binding based methods.

The activity or expression of PIF receptors may be measured using a number of conventional techniques.

The test may be an immunoassay based test. For instance, labelled antibodies (preferably a labelled antibody according to the seventh aspect of the invention) may be used in an immunoassay to evaluate receptor levels in cells or cell membranes. Such tests are particularly useful when evaluating whether or not an agents modulates PIF receptor expression, degradation or desentisation (i.e. receptor recycling). Antibodies raised against the ligand binding site may also be used to evaluate whether or not the test compound is an agonist or antagonist of the PIF receptor.

Alternatively conventional receptor binding assays (e.g. using radiolabelled PIF ligand and/or radiolabelled test compounds) may be employed. Such an assay may involve exposing membranes comprising the PIF receptor to various concentrations of [$^{35}$S]PIF in the absence or presence of a competing test compound. Bound and free radioactivity may be counted by separation of membranes from buffer by centrifugation or membrane harvesting on filters. A preferred receptor binding based assay is described in the Examples.

Alternatively a functional activity measuring PIF activity may be employed. For instance the development of cachexia may be monitored in a test animal.

Furthermore molecular biology techniques may be used to detect the PIF receptor. For instance, cDNA may be generated from mRNA extracted from tested cells or subject and primers designed to amplify test sequences used in a quantitative Polymerase Chain Reaction to amplify from cDNA.

When a subject is used (e.g. an animal model or even an animal model engineered to express human PIF receptor), the test compound should be administered to the subject for a predetermined length of time and then a sample taken from the subject for assaying PIF receptor activity or expression. The sample may for instance be blood or biopsy tissue. However the assay may be functional in which case the end point may be the monitoring of cachexia in the test subject.

Figure 4:
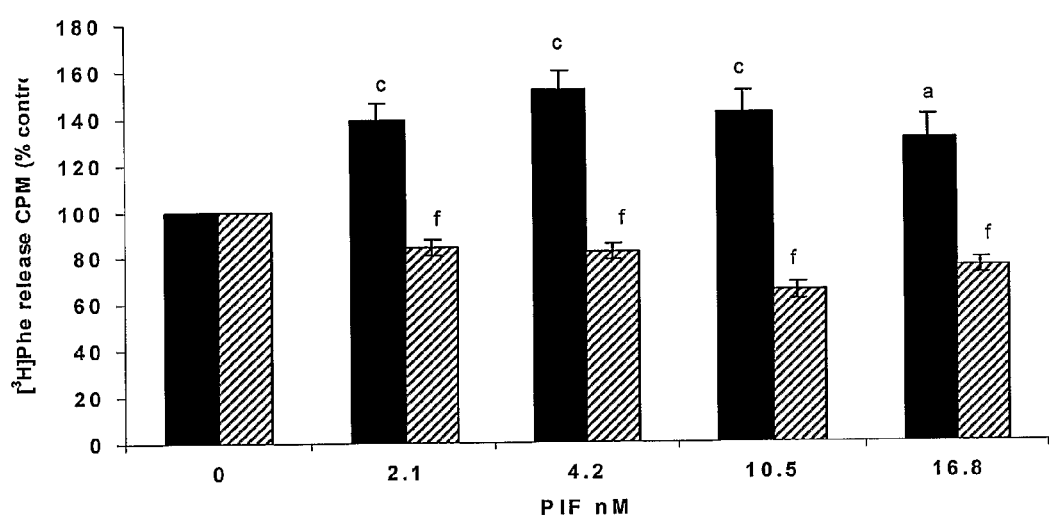
Figure 5:
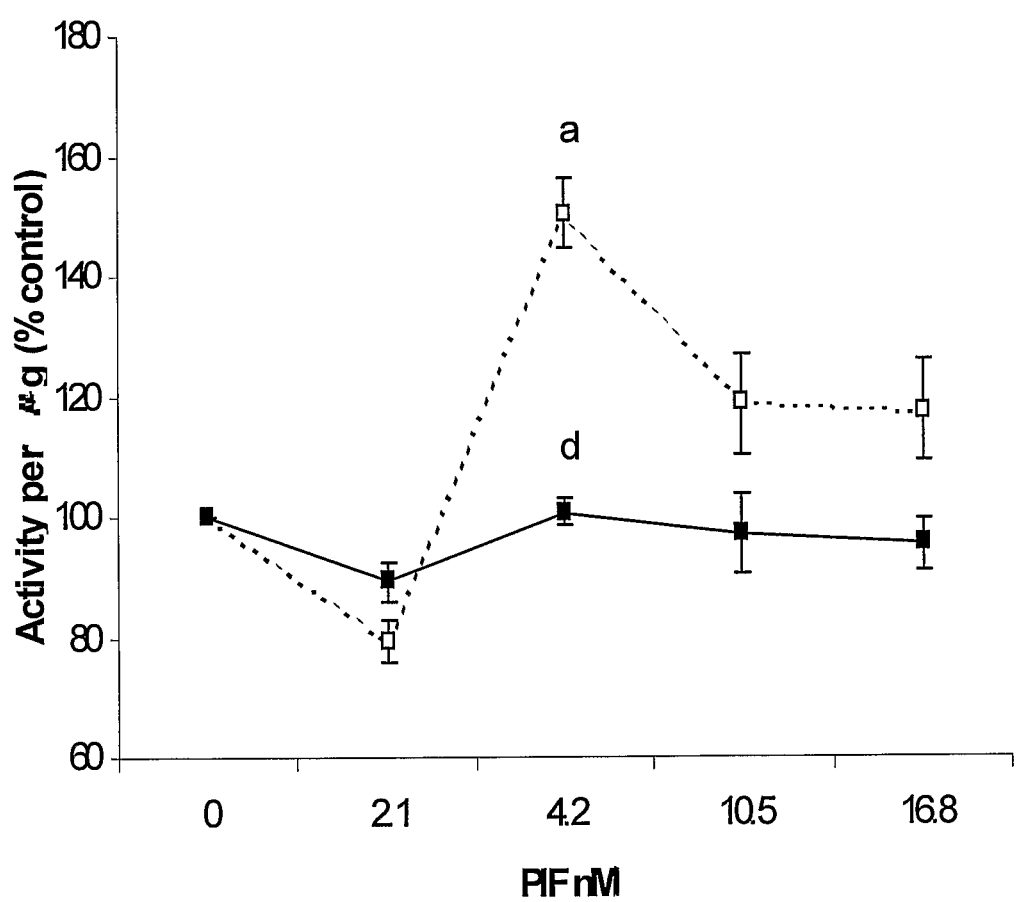
Figure 6A:
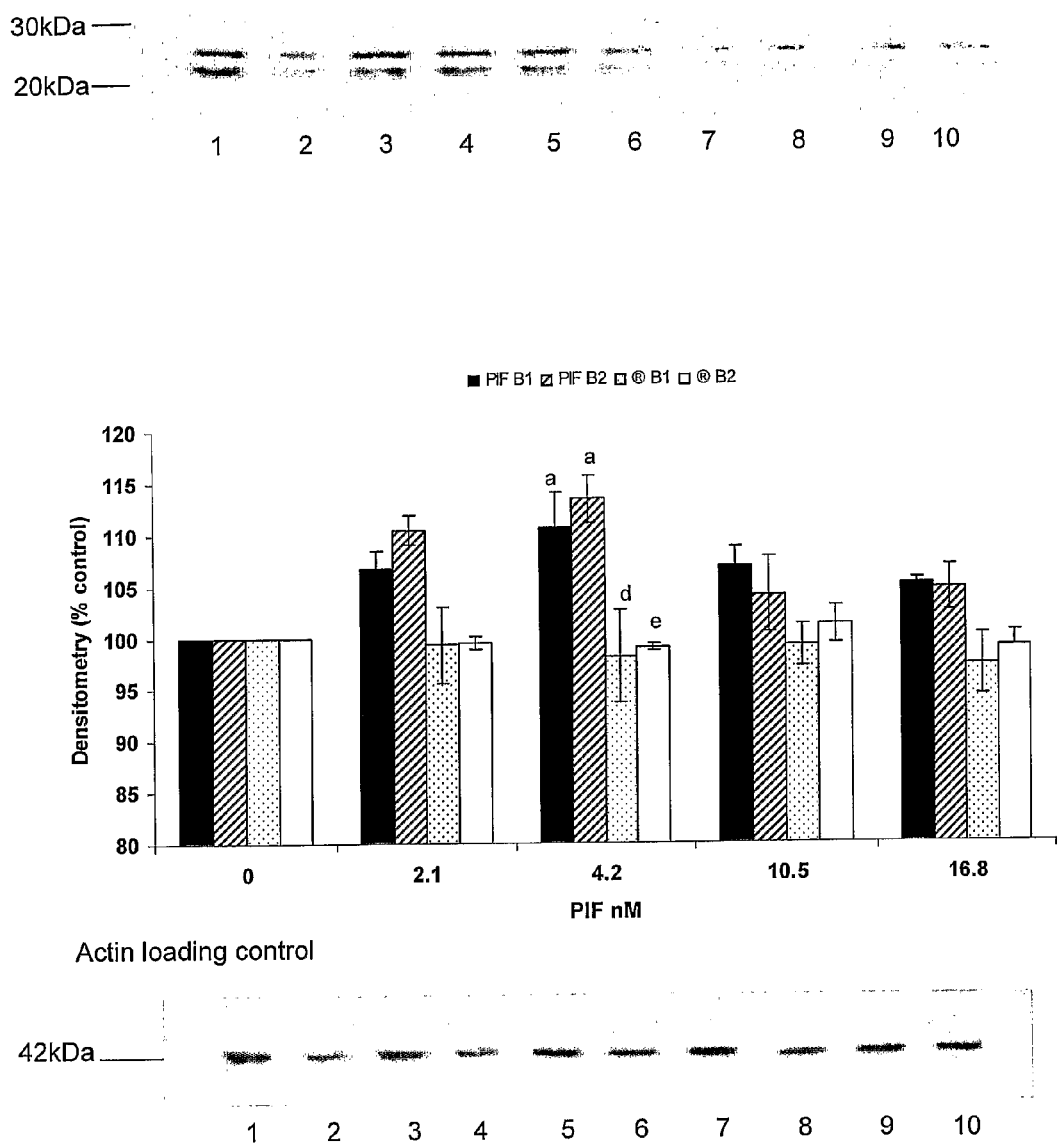
Figure 6B:
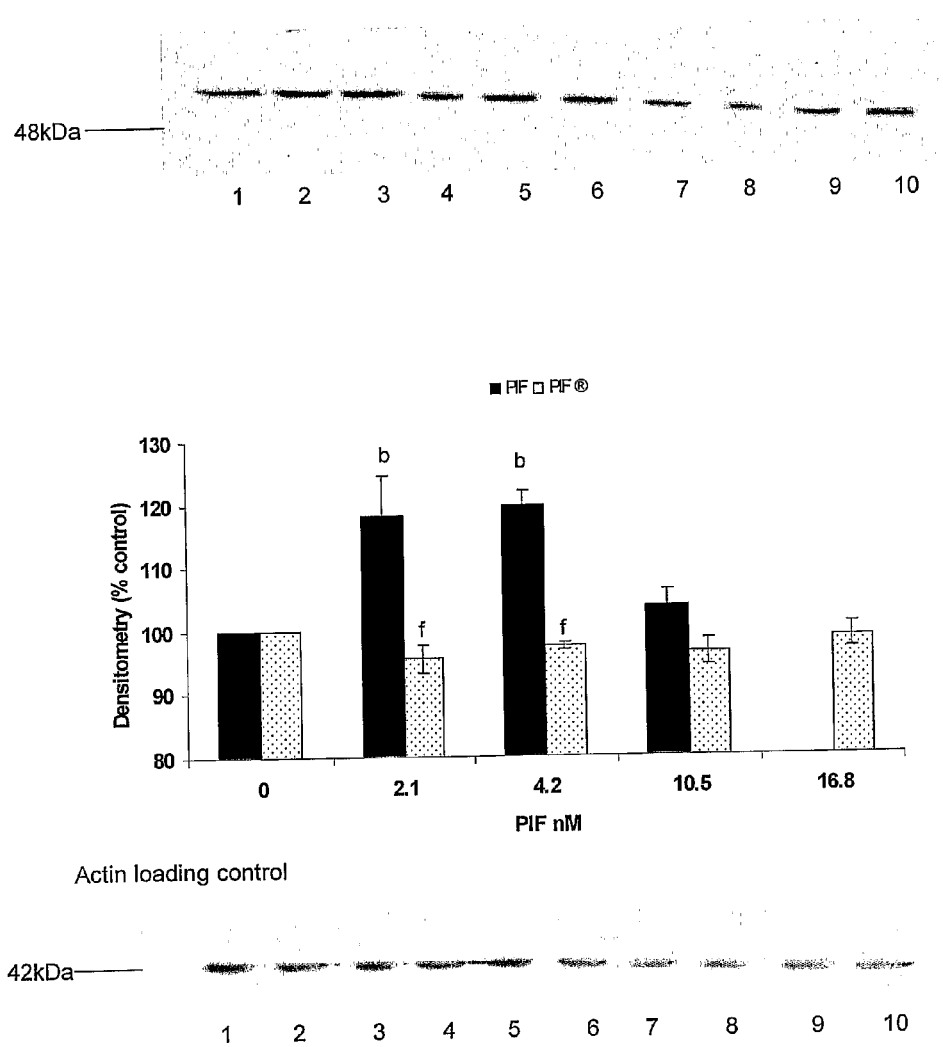
Figure 6C:
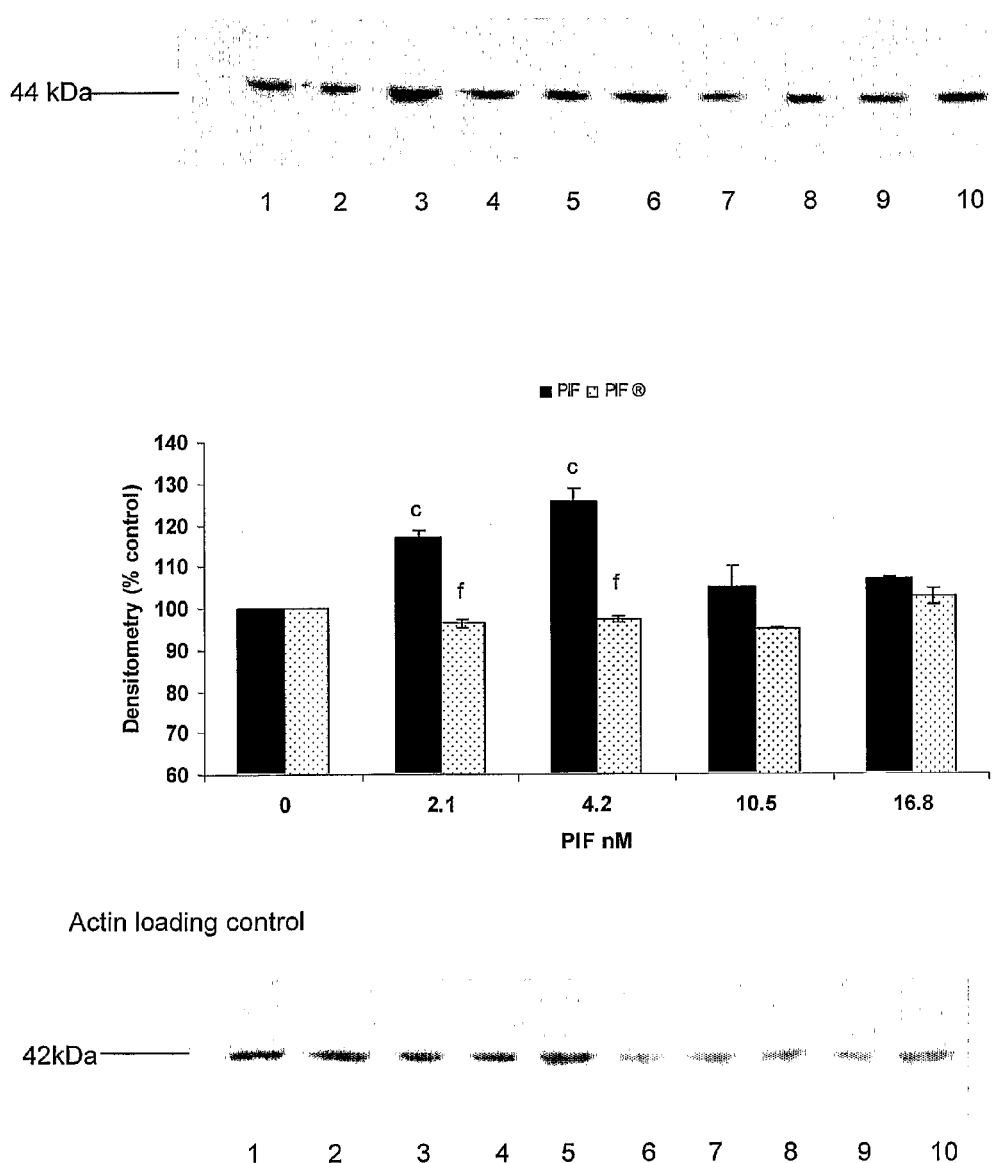
Figure 6D:
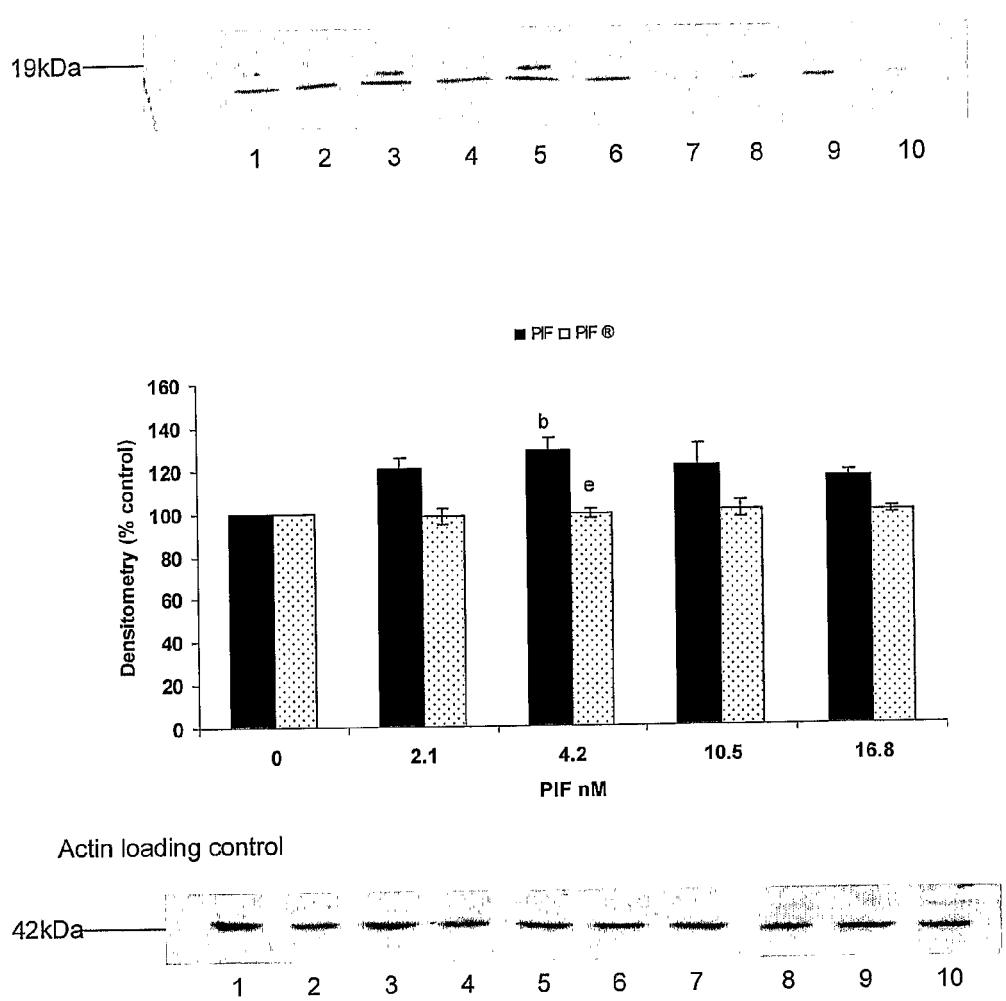
Figure 6E:
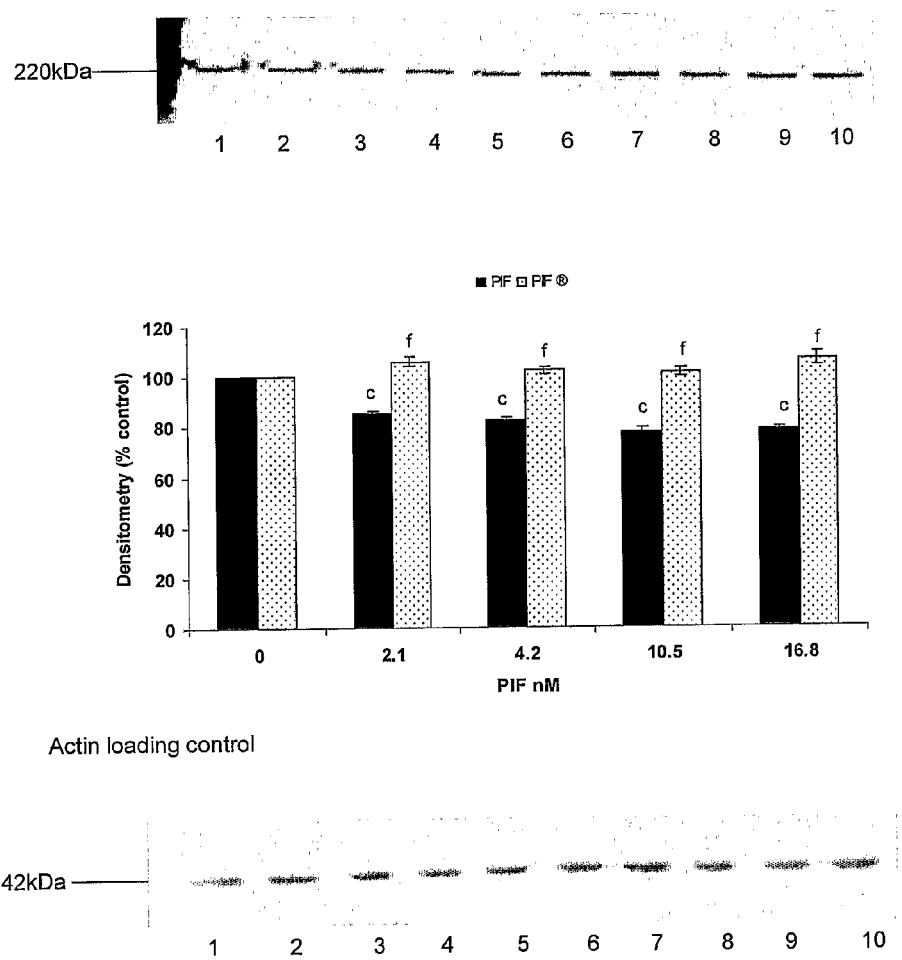

The invention will be illustrated further by Example and with reference to the following drawings, in which:

FIG. 1 shows binding of [$^3$H]peptide PIF to $C_2C_{12}$ membranes without treatment (●) or after incubation with PN Gase F (■) or O-glycosidase (▲) for 24 h;

FIGS. 2A-2B are a series of representations. FIG. 2A shows the results of electrophoresis of $C_2C_{12}$ membranes which were solubilized in 1% Triton and 50 μg of protein was loaded into each well of a 15% SDS polyacrylamide gel. Samples were electrophoresed and transferred electrophoretically to a nitrocellulose filter which had been preblocked overnight in blocking buffer (5% Marvel in PBS containing 0.1% Tween-20). The filters were blotted with increasing concentrations of [$^{35}$S] PIF in blocking bluffer for 2 h at room temperature. The concentrations of [$^{35}$S] PIF were lane 1, 5 nM; lane 2, 10 nM; lane 3, 15 nM; lane 4, 30 nM; lane 5, 60 nM; lane 6, 80 nM and lane 7, 100 nM. The filter was washed three times with PBS containing 0.1% Tween-20, air dried and processed for autoradiography. The 40 kDa bands were excised from each lane and counted directly for radioactivity (19);

FIG. 2B shows a recording of a nitrocellulose filter onto which membrane proteins which were transferred electrophoretically and blotted with [$^{35}$S] PIF 20 (30 nM), alone, lane 1 or together with 10 nM, lane 2; 20 nM, lane 3; 40 nM, lane 4; 80 nM, lane 5; 160 nM, lane 6 and 320 nM, lane 7 unlabeled PIF in blocking buffer for 2h at room temperature and processed for autoradiography;

FIG. 3 shows isolated radioactive fractions of $C_2C_{12}$ membrane which were electrophoresed on 15% SDS-PAGE where the receptor appeared as a single protein of apparent Mr 40 kDa (1—Molecular weight markers, 2,3,4—Fractions from column);

FIG. 4 shows a graphical representation of protein degradation in $C_2C_{12}$ myotubes in response to PIF in the absence (■) and presence (▨) of the N-terminal fragment of the PIF receptor (10 μM); Statistical analysis: Difference in means between groups was determined by one-way ANOVA, followed by Tukey's post-test. Difference from control is indicated as a, $p<0.05$; b, $p<0.01$ and c, $p<0.001$. Differences between peptide group and control group are indicated as d, $p<0.05$; e, $p<0.01$ and f, $p<0.001$;

FIG. 5 shows a graphical representation of chymotrypsin-like enzyme activity in $O_2O_{12}$ myotubes in response to PIF in the absence (□) and presence (■) of the N-terminal fragment of the PIF receptor (10 μM); Statistical analysis: Difference in means between groups was determined by one-way ANOVA, followed by Tukey's post-test. Difference from control is indicated as a, $p<0.05$ and difference between® peptide group and control is indicated as d, $p<0.05$;

FIG. 6A-6E are a series of representations. FIG. 6A shows a graphical representation of expression of 20S proteasome α-subunits in $O_2O_{12}$ myotubes in response to PIF and the PIF receptor peptide (Lane legend: 1 PBS control, 2 PIF 2.1 nM, 3 PIF 4.2 nM, 4 PIF 10.5 nM, 5 PIF 16.8 nM, 6® control, 7® and PIF 2.1 nM, 8® and PIF 4.2 nM, 9® and PIF 10.5 nM, 10® and PIF 16.8 nM); Statistical analysis: Difference in means between groups was determined by one-way ANOVA, followed by Tukey's post-test. Difference from control is indicated as a, $p<0.05$. Differences between® peptide group and control group are indicated as d, $p<0.05$ and e, $p<0.01$;

FIG. 6B shows a graphical representation of expression of MSS1 in $C_2C_{12}$ myotubes in response to PIF and the PIF receptor peptide (Lane legend: 1 PBS control, 2 PIF 2.1 nM, 3 PIF 4.2 nM, 4 PIF 10.5 nM, 5 PIF 16.8 nM, 6® control, 7 CO and PIF 2.1 nM, 8 and PIF 4.2 nM, 9® and PIF 10.5 nM, 10 and PIF 16.8 nM); Statistical analysis: Difference in means between groups was determined by one-way ANOVA, followed by Tukey's post-test. Difference from control is indicated as b, $p<0.05$. Differences between CO peptide group and control group are indicated as e, $p<0.01$ and f, $p<0.001$;

FIG. 6C shows a graphical representation of expression of p42 in $C_2C_{12}$ myotubes in response to PIF and the PIF receptor peptide (Lane legend: 1 PBS control, 2 PIF 2.1 nM, 3 PIF 4.2 nM, 4 PIF 10.5 nM, 5 PIF 16.8 nM, 6® control, 7® and PIF 2.1 nM, 8® and PIF 4.2 nM, 9® and PIF 10.5 nM, 10 and PIF 16.8 nM); Statistical analysis: Difference in means between groups was determined by one-way ANOVA, followed by Tukey's post-test. Difference from control is indicated as a, $p<0.05$. Differences Between® peptide group and control group are indicated as d, $p<0.05$ and e, $p<0.01$;

FIG. 6D shows a graphical representation of expression of $E2_{14k}$ in $C_2C_{12}$ myotubes in response to PIF and the PIF receptor peptide (Lane legend: 1 PBS control, 2 PIF 2.1 nM, 3 PIF 4.2 nM, 4 PIF 10.5 nM, 5 PIF 16.8 nM, 6® control, 7® and PIF 2.1 nM, 8® and PIF 4.2 nM, 9® and PIF 10.5 nM, 10® and PIF 16.8 nM); Statistical analysis Difference in means between groups was determined by one-way ANOVA, followed by Tukey's post-test. Difference from control is indicated as b, $p<0.01$. Differences Between® peptide group and control group are indicated as e, $p<0.01$;

FIG. 6E shows a representation of Myosin expression in $C_2C_{12}$ myotubes in response to PIF and the PIF receptor peptide (Lane legend: 1 PBS control, 2 PIF 2.1 nM, 3 PIF 4.2 nM, 4 PIF 10.5 nM, 5 PIF 16.8 nM, 6® control, 7® and PIF 2.1 nM, 8 and PIF 4.2 nM, 9® and PIF 10.5 nM, 10® and PIF 16.8 nM); Statistical analysis: Difference in means between groups was determined by one-way ANOVA, followed by Tukey's post-test. Difference from control is indicated as a, $p<0.05$. Differences Between® peptide group and control group are indicated as d, $p<0.05$ and e, $p<0.01$.

Figure 7:
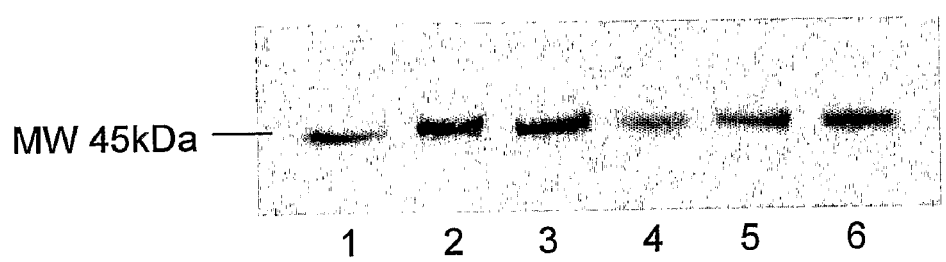
Figure 8:
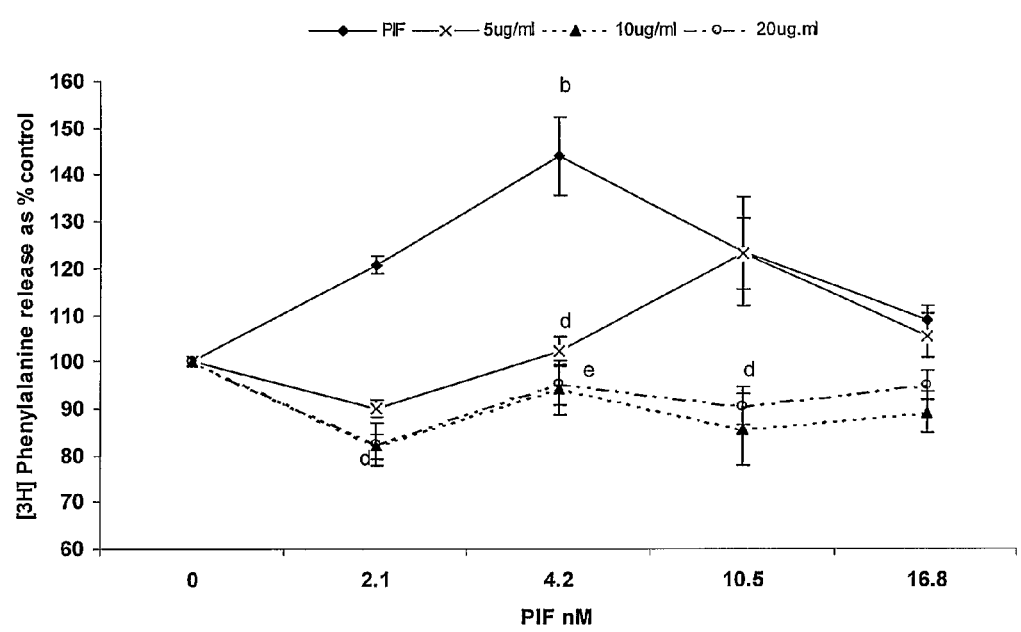
Figure 10B:
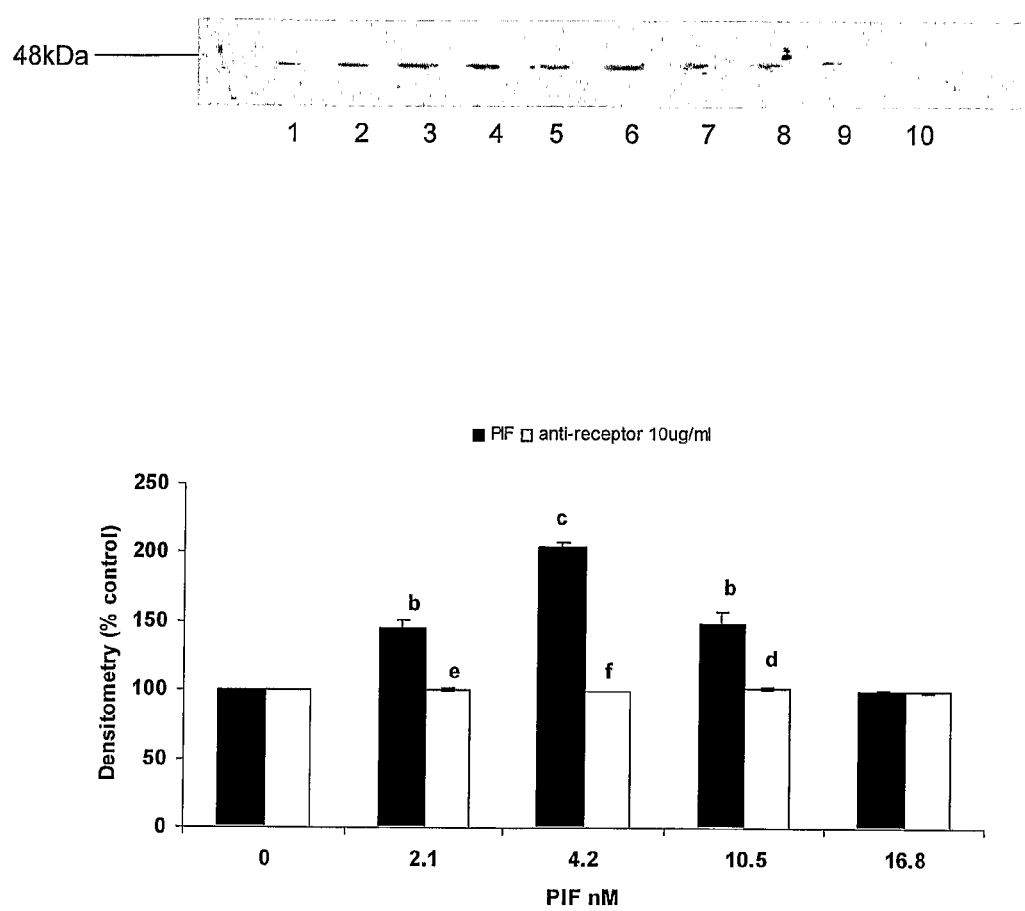
Figure 10C:
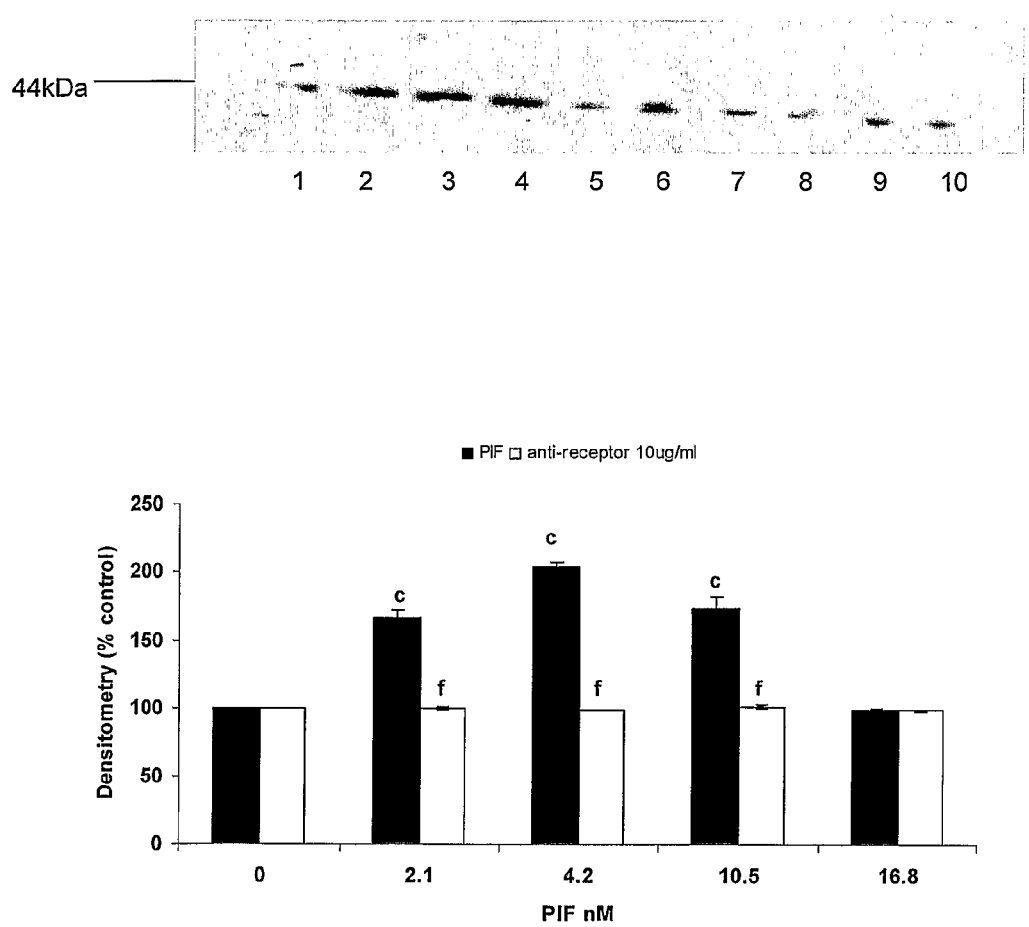
Figure 10D:
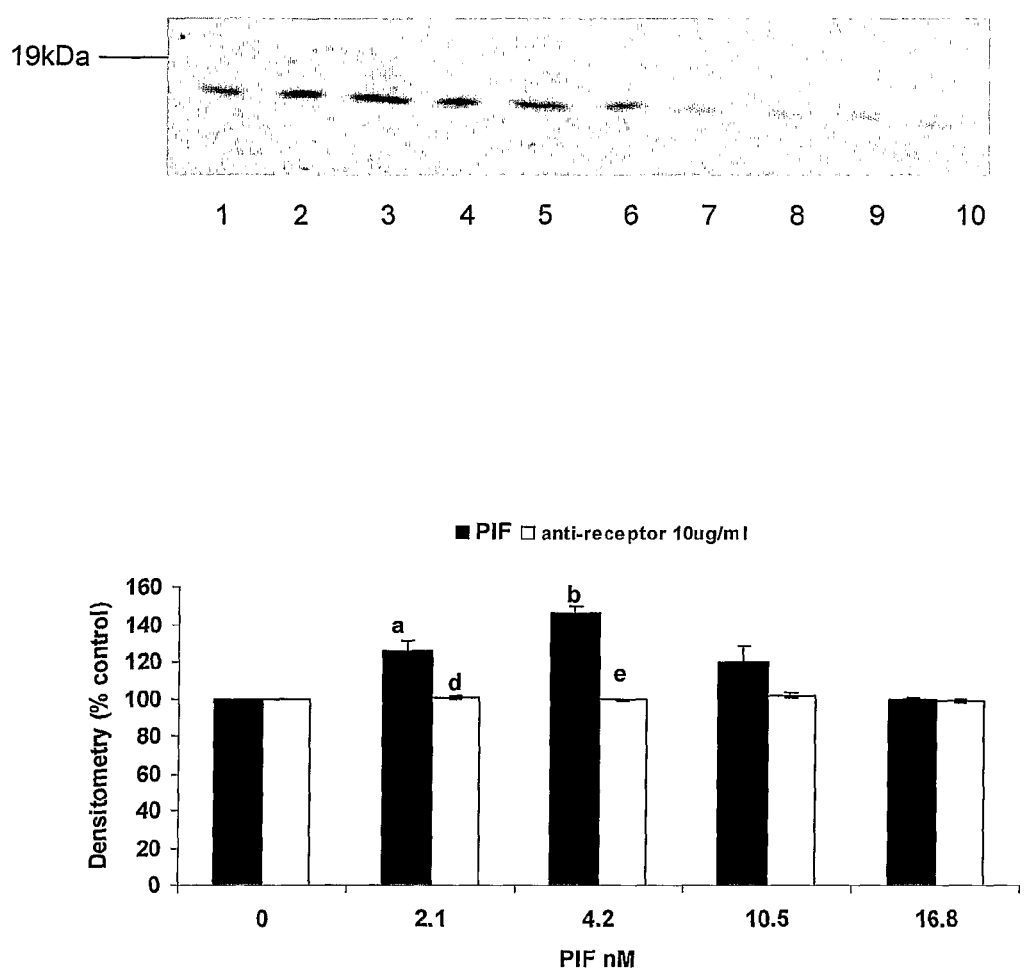

FIG. 7 shows a photograph of a Western Blot using anti-receptor antisera performed after purification of the antibody by adding 50% saturated ammonium sulphate followed by Protein-A column chromatography:
1 Purified receptor 5 μg protein
2 Purified receptor 10 μg protein
3 Purified receptor 20 μg protein
4 Crude membrane fraction 20 μg protein
5 Crude membrane fraction 30 μg protein
6 Crude membrane fraction 40 μg protein FIG. 8 shows a graphic representation of the effect of the antibody to the PIF receptor at concentrations between 5 and 15 μg/ml on protein degradation in vitro induced by PIF; Statistical analysis: Difference in means between groups was determined by one-way ANOVA, followed by Tukey's post-test. Difference from control is indicated as b, $p<0.01$, differences between control and anti-receptor are indicated as d, $p<0.05$ and e, $p<0.01$;

FIG. 9 shows graphic representation of the effect of the antibody to the PIF receptor on the PIF-induced increase in chymotrypsin-like enzyme activity; Statistical analysis: Difference in means between groups was determined by one-way ANOVA, followed by Tukey's post-test. Differences from control is indicated as c, $p<0.001$, differences between control and anti-receptor are indicated as d, $p<0.05$ and e, $p<0.01$;

FIGS. 10A-10E are a series of representations. FIG. 10A shows a graphical representation of expression of 20S proteasome α-subunits in $C_2C_{12}$ myotubes in response to PIF and anti-receptor antibody (10 μg/ml) (Lane legend: 1 PBS control, 2 PIF 2.1 nM, 3 PIF 4.2 nM, 4 PIF 10.5 nM, 5 PIF 16.8 nM, 6 αPIF Ab control, 7 αPIF Ab and PIF 2.1 nM, 8 αPIF AB and PIF 4.2 nM, 9 αPIF Ab and PIF 10.5 nM, 10 αPIF Ab® and PIF 16.8 nM); Statistical analysis: Difference in means between groups was determined by one-way ANOVA, followed by Tukey' s post-test. Differences from control are indicated as c, $p<0.001$. Differences between anti-receptor 10 mg/ml and PIF are indicated as f, $p<0.001$;

FIG. 10B shows a graphical representation of expression of MSS1 in $C_2C_{12}$ myotubes in response to PIF and anti-receptor antibody (10 μg/ml) (Lane legend: 1 PBS control, 2 PIF 2.1 nM, 3 PIF 4.2 nM, 4 PIF 10.5 nM, 5 PIF 16.8 nM, 6 αPIF Ab control, 7 αPIF Ab and PIF 2.1 nM, 8 αPIF AB and PIF 4.2 nM, 9 αPIF Ab and PIF 10.5 nM, 10 αPIF Ab® and PIF 16.8 nM); Statistical analysis: Difference in means between groups was determined by one-way ANOVA, followed by Tukey's post-test. Differences from control are indicated as b, $p<0.01$; c, $p<0.001$. Differences between anti-receptor 10 mg/ml and PIF are indicated as d, $p<0.05$; e, $p<0.01$ and f, $p<0.001$;

FIG. 10C shows a graphical representation of expression of p42 in $C_2C_{12}$ myotubes in response to PIF and anti-receptor antibody (10 μg/ml) (Lane legend: 1 PBS control, 2 PIF 2.1 nM, 3 PIF 4.2 nM, 4 PIF 10.5 nM, 5 PIF 16.8 nM, 6 αPIF Ab control, 7 αPIF Ab and PIF 2.1 nM, 8 αPIF AB and PIF 4.2 nM, 9 αPIF Ab and PIF 10.5 nM, 10 αPIF Ab® and PIF 16.8 nM); Statistical analysis: Difference in means between groups was determined by one-way ANOVA, followed by Tukey's post-test. Differences from control are indicated as c, $p<0.001$. Differences between anti-receptor 10 mg/ml and PIF are indicated as f, $p<0.001$;

FIG. 10D shows a graphical representation of expression of $E2_{14k}$ in $C_2C_{12}$ myotubes in response to PIF and anti-receptor antibody (10 μg/ml) (Lane legend: 1 PBS control, 2

Figure 10E:
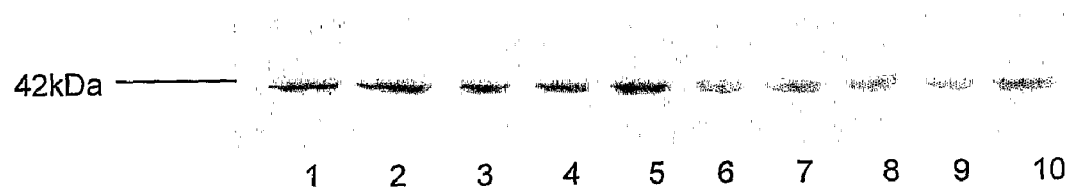
Figure 11A:
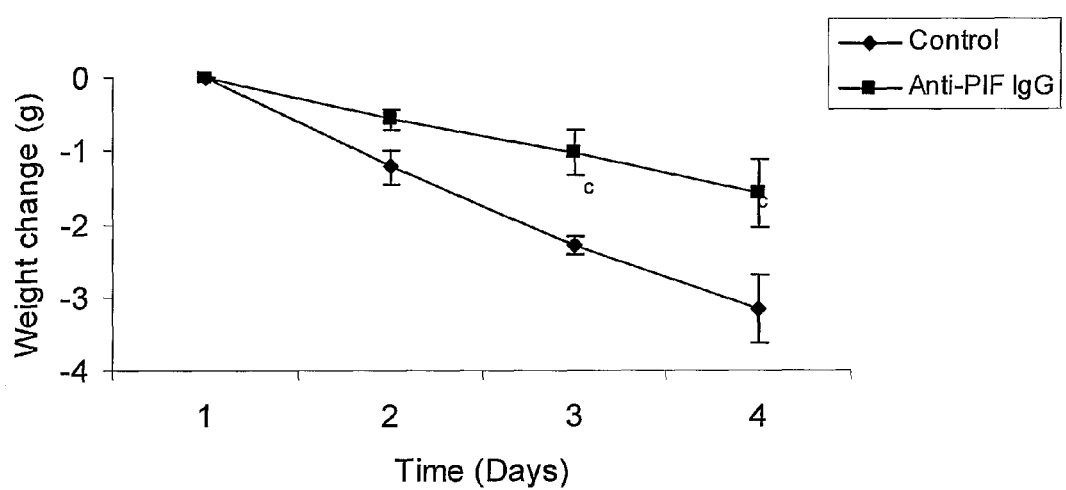
Figure 11B:
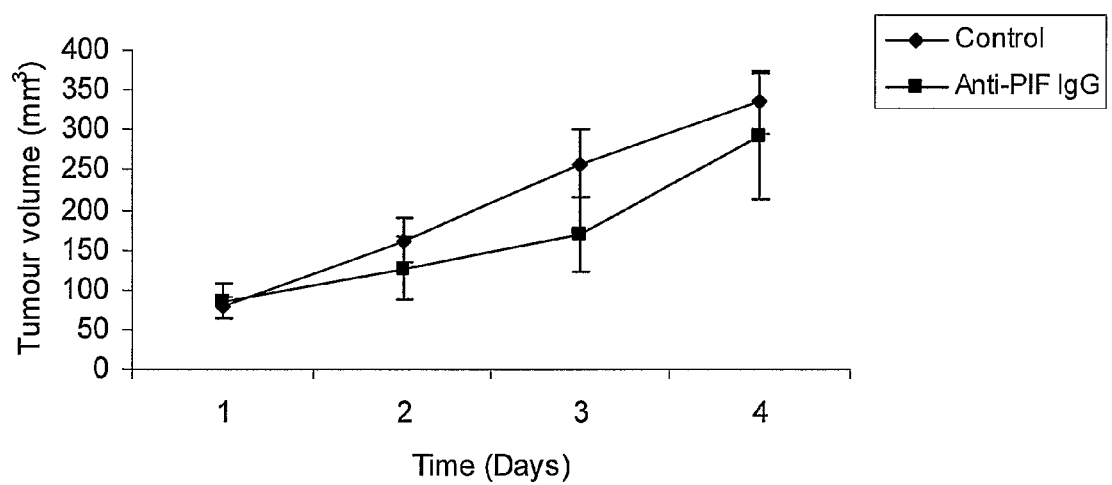
Figure 12A:
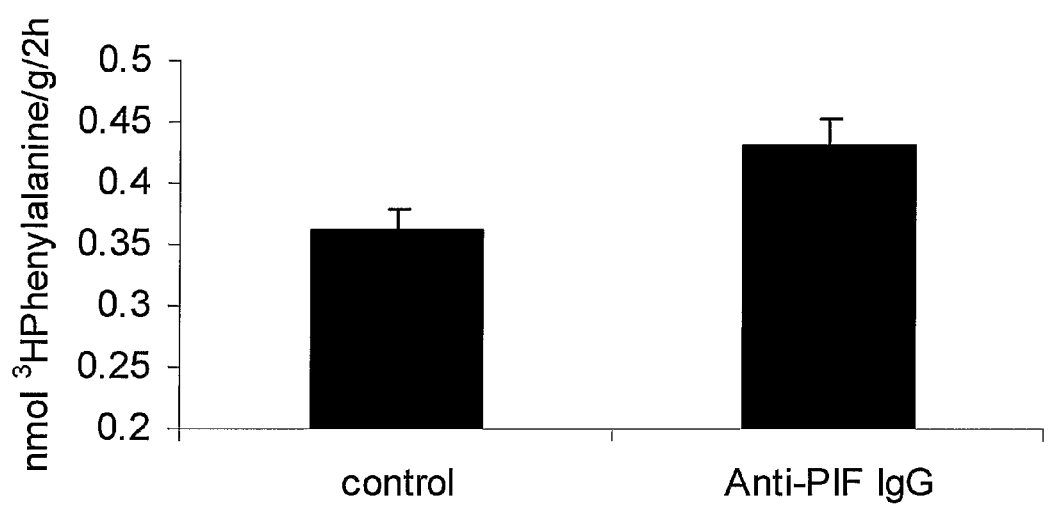
Figure 12B:
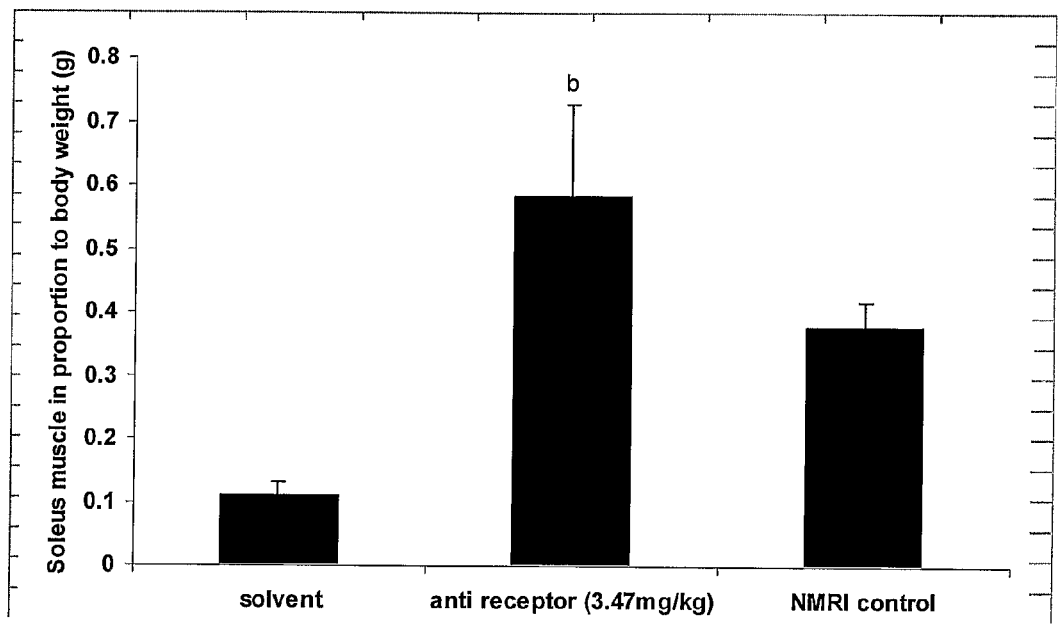
Figure 12C:
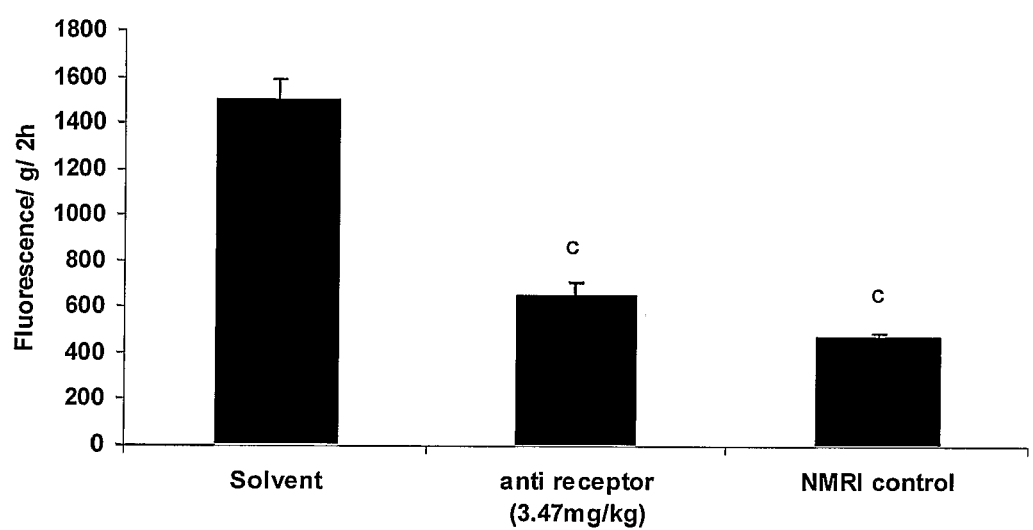
Figure 12D:
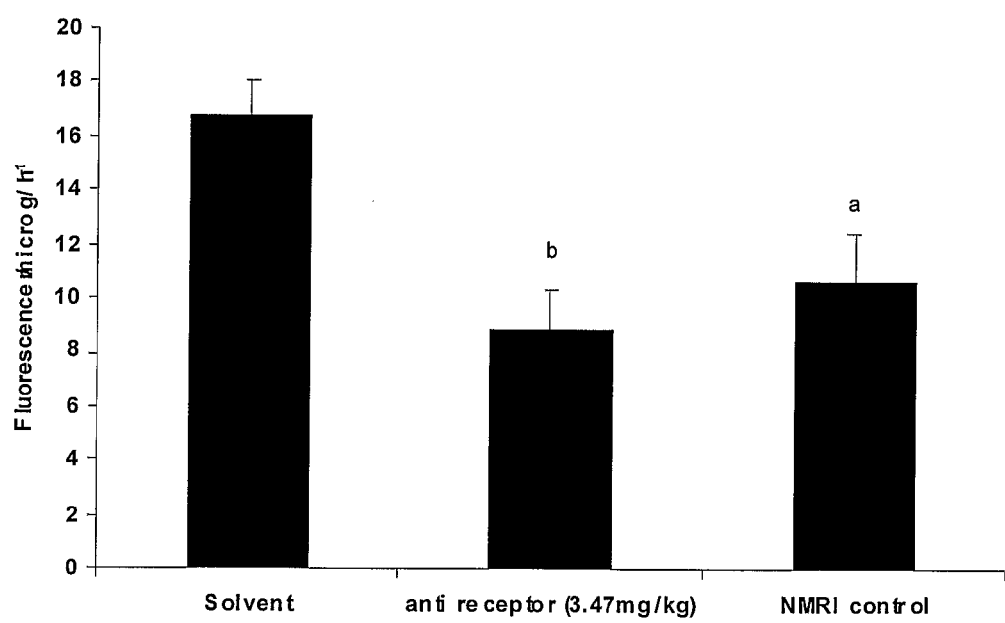
Figure 13B:
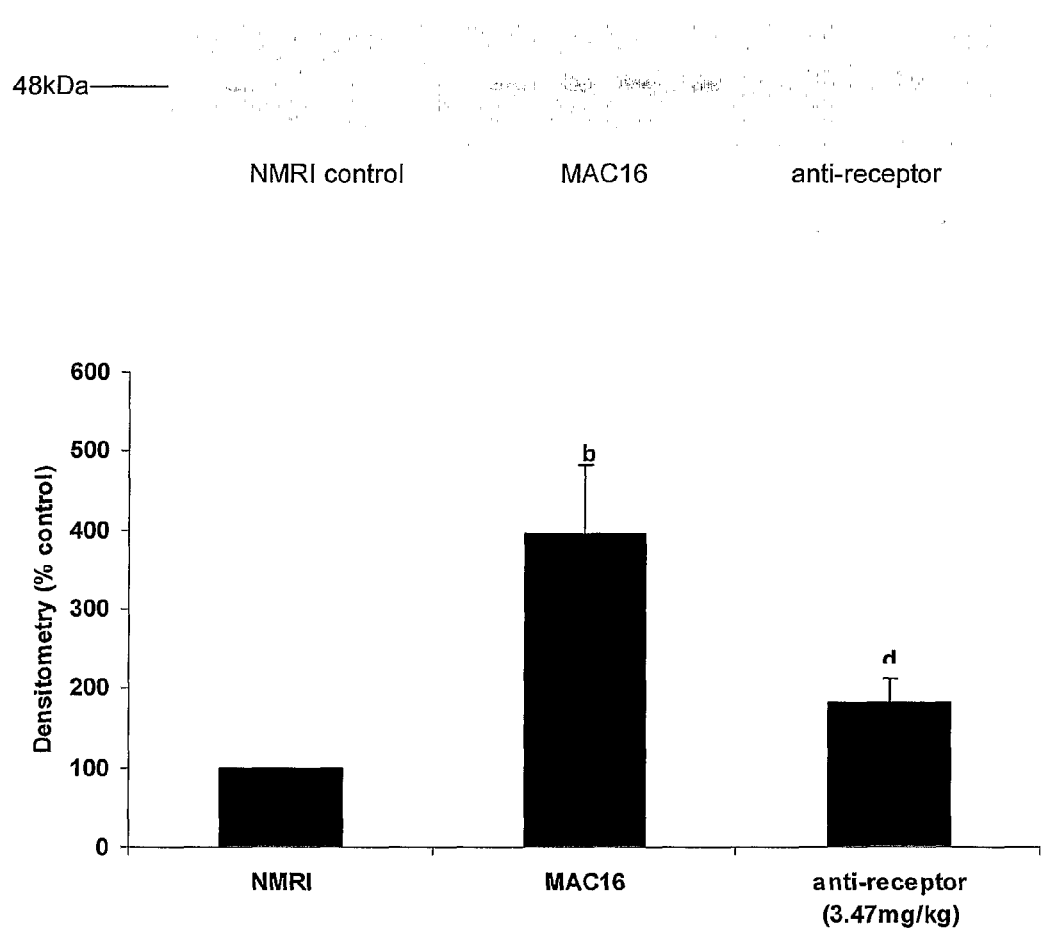
Figure 13C:
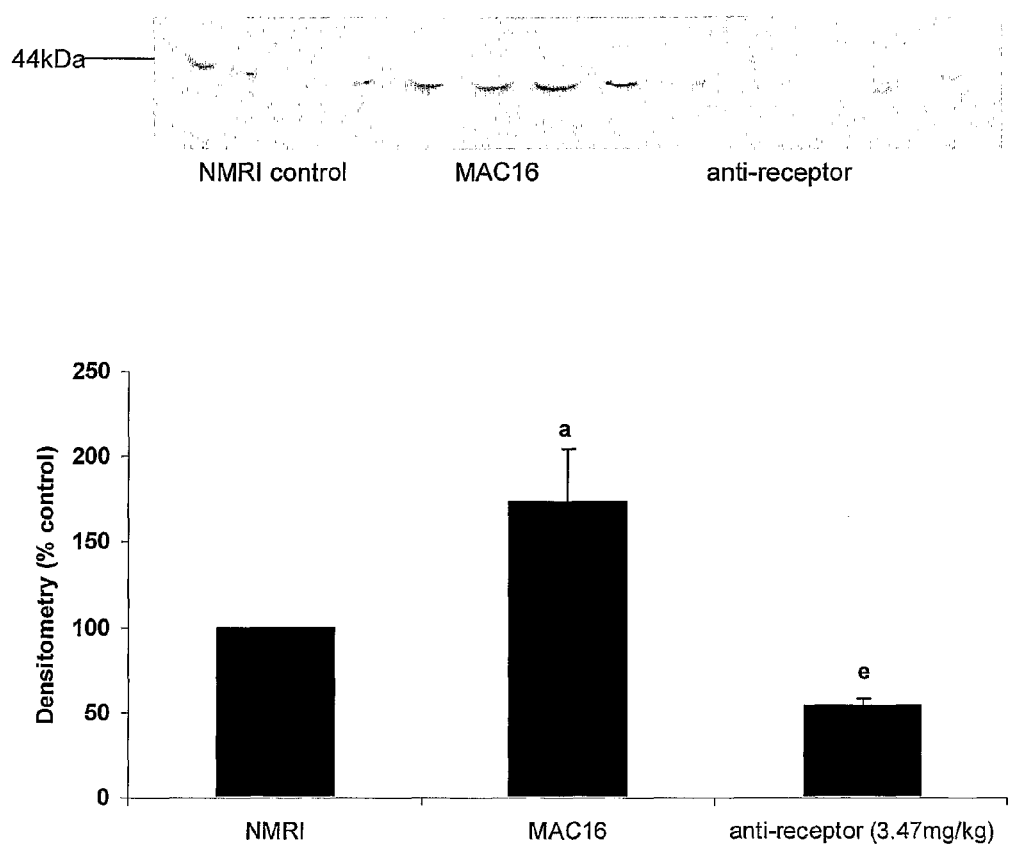
Figure 13D:
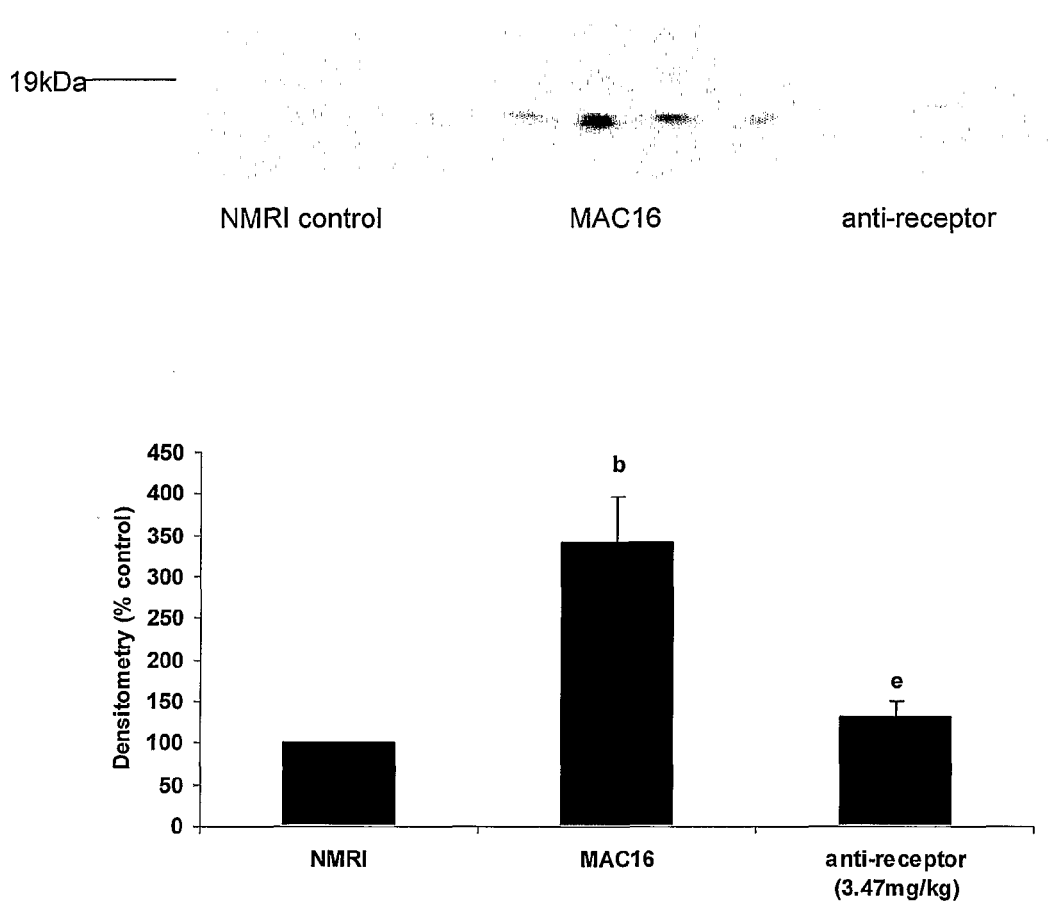
Figure 13F:
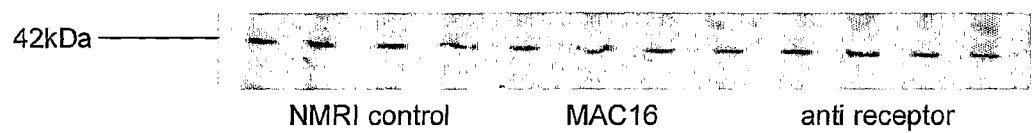

PIF 2.1 nM, 3 PIF 4.2 nM, 4 PIF 10.5 nM, 5 PIF 16.8 nM, 6 αPIF Ab control, 7 αPIF Ab and PIF 2.1 nM, 8 αPIF AB and PIF 4.2 nM, 9 αPIF Ab and PIF 10.5 nM, 10 αPIF Ab and PIF 16.8 nM); Statistical analysis: Difference in means between groups was determined by one-way ANOVA, followed by Tukey's post-test. Differences from control are indicated as a, $p<0.05$; b, $p<0.01$. Differences between anti-receptor 10 mg/ml and PIF are indicated as d, $p<0.05$ and e, $p<0.01$;

FIG. 10E represents an Actin blot as a loading control to show that equal amounts of protein (PIF and anti-receptor antibody, 10 μg/ml) have been loaded in FIG. A to D. (Lane legend: 1 PBS control, 2 PIF 2.1 nM, 3 PIF 4.2 nM, 4 PIF 10.5 nM, 5 PIF 16.8 nM, 6 αPIF Ab control, 7 αPIF Ab and PIF 2.1 nM, 8 αPIF AB and PIF 4.2 nM, 9 αPIF Ab and PIF 10.5 nM, 10 αPIF Ab and PIF 16.8 nM);

FIGS. 11A-11B are a series of representations. FIG. 11A shows weight change in MAC16 tumour bearing mice treated daily i.p. with and without Anti-PIF IgG; Statistically significant c, $P<0.001$ from control by one-way ANOVA followed by Tukey's post-test;

FIG. 11B shows tumour volume in MAC16 tumour bearing mice treated with and without Anti-PIF IgG;

FIGS. 12A-12D are a series of representations. FIG. 12A shows protein synthesis in the soleus muscle of MAC16 Tumour bearing mice treated with and without Anti-PIF IgG; Statistically significant a, $P<0.05$ from control by one-way ANOVA followed by Tukey's post-test;

FIG. 12B shows soleus muscle weight in proportion to body weight compared with solvent treated controls; Statistical analysis: Difference in means between groups was determined by one-way ANOVA, followed by Tukey's post-test. Differences from solvent are indicated as b, $p<0.01$;

FIG. 12C is a graphical representation of Tyrosine release assay results for PIF receptor antibody (3.47 mg/kg) in vivo; Statistical analysis: Difference in means between groups was determined by one-way ANOVA, followed by Tukey's post-test. Differences from solvent are indicated as c, $p<0.001$;

FIG. 12D shows the effect of anti-receptor antibody (3.47 mg/kg) on chymotrypsin-like enzyme activity in gastrocnemius muscle; Statistical analysis: Difference in means between groups was determined by one-way ANOVA, followed by Tukey's post-test. Differences from solvent are indicated as a, $p<0.05$ and b, $p<0.01$;

FIGS. 13A-13F are a series of representations. FIG. 13A shows a graphical representation of expression of 20S proteasome α-subunits in gastrocnemius muscle in response to anti- receptor antibody (3.47 mg/kg); Statistical analysis: Difference in means between groups was determined by one-way ANOVA, followed by Tukey's post-test. Difference from control is indicated as c, $p<0.001$. Difference between anti-receptor and MAC16 group is indicated as f, $p<0.001$;

FIG. 13B shows a graphical representation of expression of MSS1 in gastrocnemius muscle in response to anti-receptor antibody (3.47 mg/kg); Statistical analysis: Difference in means between groups was determined by one-way ANOVA, followed by Tukey's post-test. Difference from control is indicated as b, $p<0.01$. Difference between anti-receptor and MAC16 group is indicated as d, $p<0.05$;

FIG. 13C shows a graphical representation of expression of p42 in gastrocnemius muscle in response to anti-redeptor antibody (3.47 mg/kg); Statistical analysis: Difference in means between groups was determined by one-way ANOVA, followed by Tukey's post-test. Difference from control is indicated as a, $p<0.05$. Difference between anti-receptor and MAC16 group is indicated as e, $p<0.001$;

FIG. 13D shows a graphical representation of expression of $E2_{14k}$ in response to anti-receptor antibody (3.47 mg/kg);

Statistical analysis: Difference in means between groups was determined by one-way ANOVA, followed by Tukey's post-test. Difference from control is indicated as b, $p<0.01$. Difference between anti-receptor and MAC16, group is indicated as e, $p<0.001$;

FIG. 13E shows a representation of Myosin expression in gastrocnemius muscle in response to anti-receptor antibody (3.47 mg/kg); Statistical analysis: Difference in means between groups was determined by one-way ANOVA, followed by Tukey's post-test. Difference from control is indicated as b, $p<0.01$. Difference between anti-receptor and MAC16 group is indicated as d, $p<0.05$;

FIG. 13F represents an actin control loading blot expression in gastrocnemius muscle in response to anti receptor (3.47 mg/kg) to show that equal amounts of protein have been loaded in FIGS. 13A to 13E.

EXAMPLE 1

The invention is based upon the following experiments that were conducted to investigate, and characterise PIF binding sites in various tissues.

1.1 Materials and Methods

Chemicals: Bovine fetal serum, RPMI1640 and Dulbecco's Modified Eagles Medium (DMEM) were purchased from GIBCO-BRL (Scotland, United Kingdom).

MAC16 monoclonal antibody was isolated from the culture medium of a hybridoma cell line (Todorov, P. T., McDevitt, T. M., Cariuk, P., Coles, B., Deacon, M. and Tisdale, M. J. Induction of muscle protein degradation and weight loss by a tumor product. Cancer Res., 56: 1256-1261, 1996.) using a protein A-Sepharose column.

L-$[2,6-^3H]$ phenylalanine (specific activity 54 Cimmol$^{-1}$) and $Na_2^{35}SO_4$ (specific activity 10-100 mCimmol$^{-1}$) were purchased from Amersham Int., (Buckinghamshire, United Kingdom).

All chemicals were purchased from Sigma Chemical Co., (Dorset, United Kingdom). Optiphase Hisafe 3 scintillation fluid was supplied by Fisons (Loughborough, United Kingdom).

Cell culture and tumor propagation: The $C_2C_{12}$ mouse myoblast cell line was grown in 60×15 mm petri dishes in 3 ml DMEM supplemented with 12% fetal bovine serum, 1% non-essential amino acids and 1% penicillin-streptomycin in a humidified atmosphere of 5% $CO_2$ in air at 37° C. All experiments with myoblasts were performed on cells in the subconfluent state. MAC16 cells were maintained in RPMI 1640 medium containing 5% fetal bovine serum at 37° C. under an atmosphere of 5% $CO_2$ in air. Normal human muscle cells, Hs94MU, were obtained from the European Collection of Cell Cultures (Wiltshire, United Kingdom) and were maintained in Dulbecco's Modified Eagles medium containing 2 mM glutamine and 10% fetal bovine serum under an atmosphere of 5% $CO_2$ in air. For biosynthetic labeling the cell suspension contained $Na_2^{35}SO_4$ (1 μCiml$^{-1}$) for 48 h in RPMI 1640 medium containing 1.5% dialyzed fetal bovine serum.

Pure strain NMRI mice, bred in the inventors' own colony, were implanted in the flank with fragments of the MAC16 tumor, excised from donor animals with established weight loss. Weight loss is evident 10-12 days after transplantation, when the tumor becomes palpable. Fragments of the MAC13 tumor were implanted by the same procedure. This tumor produces no weight loss during growth.

Purification of labeled PIF Cells: were sedimented by low speed centrifugation (1500 rpm for 5 min on a bench-top centrifuge). The cell pellet was resuspended in 1 ml of 10 mM Tris. HCl, pH 8.0, containing 0.5 mM phenylmethylsulfonyl fluoride (PMSF), 0.5 mM EGTA and 1 mM dithiothreitol and dissociated using an ultrasonic oscillator. After centrifugation (15,000 rpm for 20 min) solid ammonium sulfate (38% w/v) was added slowly to the supernatant with stirring, and the mixture was stored overnight at 4° C. Salt was removed from the sample by ultrafiltration with an Amicon filtration cell containing a membrane filter with a molecular weight cut-off of 10,000 against the sonicating buffer. The concentrated sample was loaded onto an affinity column containing MAC16 monoclonal antibody (Todorov, et al. Cancer Res. supra) coupled to Affi-Gel Hz (Bio-Rad, Hemel Hempstead, United Kingdom) equilibrated with 10 mM Tris. HCl, pH 8.0. After overnight circulation at a flow rate of 5 ml h$^{-1}$, the column was washed with 10 mM Tris. HCl, pH 8.0, and the retained material was eluted with 100 mM glycine HCl, pH 2.5. After neutralization with 1M Tris. HCl, pH 8.0, the fractions containing radioactivity were concentrated by Amicon filtration against water and further purified by hydrophobic chromatography using a Brownlee Aquopore RP-300 $C_B$ column and an acetonitrile in water gradient as described (Todorov, et al. Cancer Res. supra and Todorov, et al. Nature. supra). Material eluting at 55% acetonitrile was concentrated against water using an Amicon filtration cell containing a membrane filter with a molecular weight cut-off of 10,000.

Membrane isolations: Sarcolemma membranes were prepared from gastrocnemius muscle of mice bearing either the MAC16 or MAC13 tumor essentially as described (Ohlendieck, K., Ervasti, J. M., Snook, J. B. and Campbell, K. P. Dystrophin-glycoprotein complex is highly enriched in isolated skeletal muscle sarcolemma. J. Cell Biol., 112: 135-148, 1991). Briefly gastrocnemius muscle (5 g) was excised and homogenized in 20 mM sodium pyrophosphate, 20 mM sodium phosphate, 1 mM $MgCl_2$, 0.303M sucrose, 0.5 mM EDTA, pH 7.0, containing the protease inhibitors aprotinin (76.8 nM), leupeptin (1.1 µM), pepstatin A (0.7 µM), benzamide (0.83 mM), iodoacetamide (1 mM) and PMSF (0.23 mM). The homogenate was centrifuged at 30,000×g for 30 min. Light mucrosomes were obtained from the supernatant after adding solid KCl to a final concentration of 0.6M, followed by centrifugation at 142,000 g for 35 min. The pellets were suspended in 0.303M sucrose, 20 mM Tris-maleate, pH 7.0 (buffer B), treated again with KCl, followed by centrifugation as described. The final pellets of light microsomes were resuspended in buffer B (6 ml) containing 0.6M KCl and 1 ml aliquots were loaded onto 7 ml of 0.878M sucrose, 0.6M KCl, 20 Mm Tris-maleate, pH 7.0 in centrifuge tubes and centrifuged at 112,000 g for 17 h. The crude surface membrane fraction at the 0303M/0.878M sucrose interface was collected and resuspended in buffer B and stored frozen at −80° C. Sarcolemma membranes from pig muscle were prepared by the same procedure.

For $C_2C_{12}$ cell membranes: homogenization was carried out in 20 mM HEPES, pH 7.4, 1 mM EDTA, 0.5 mM PMSF and 1 mM DTT at 4° C. The homogenate was centrifuged at 20,000 rpm for 30 min and washed with the same buffer. The pellet was used for binding studies. Adipocyte plasma membranes were prepared from adipocytes isolated from epididymal adipose tissue of male BKW mice by a modification of the protocol of Belsham et al. (Belsham, G. J., Denton, R. M. and Tanner, M. J. A. Use of a novel rapid preparation of fat-cell plasma membranes employing percoll to investigate the effects of insulin and adrenaline on membrane protein phosphorylation within intact fat cells. Biochem. J., 192: 457-467, 1980.). Essentially plasma membranes were isolated from other components of a cell homogenate using a self-forming Percoll gradient. The membrane fractions were washed in a NaCl buffer, diluted in 10 mM Tris. HCl, pH 7.4, 250 mM sucrose, 2 mM EGTA and 4 µM PMSF at 1-2 mg ml$^{-1}$, snap frozen in liquid nitrogen and stored at −70° C. until use. Hepatocyte plasma membranes were purified by a scheme similar to that for adipocytes (Belsham et al. Supra), which had been modified for hepatocytes (Nakamura, T., Tomomura, A., Noda, C., Shimoji, M. and Ichihara, A. Acquisition of a β-adrenergic response by adult rat hepatocytes during primary culture. J. Biol. Chem., 258: 9283-9289, 1983).

Binding studies: Membranes (200 µg protein suspended in 200 µl PBS) were incubated for 24 h at 4° C. with various concentrations of [$^{35}$S]PIF in 50 µl PBS as detailed in the figure legends. Bound and free radioactivity was separated by centrifugation for 5 min at 13,000 g.

Determination of affinity constant (Kaff) of PIF for monoclonal antibody: The affinity of an antibody for its antigen can be estimated if bound and free antigen can be measured when a fixed trace amount of antigen is allowed to bind to serial dilutions of antibody. The antibody concentration at half-maximal binding is a measure of affinity.

Monoclonal antibody was purified from the tissue culture supernatant of a hybridoma as described (Todorov, et al. Cancer Res. supra) using a Protein A column. Serial dilutions of the antibody were made in the dilutent 0.25M Tris-HCl, pH 8.5 with 2% calf serum and 1% Tween 20 to a final dilution factor of $10^4$-$10^5$. PIF was iodinated as described ((Todorov, et al. Nature. supra) and diluted in the above diluent such that 50 µl contained 2×$10^4$ cpm. The diluted monoclonal antibody (100 µl) was dispensed into tubes followed by $^{125}$I PIF (50 µl) and the tubes were incubated for 2 h at room temperature. Then Protein A-sepharose (100 µl) was added and the tubes were shaken for a further 2 h. Dilutent (3 ml) was added and the tubes were centrifuged, decanted and washed with another 3 ml of dilutent. The final sedimented solid phase was counted in a gamma counter.

Competitive binding of [$^{35}$S]PIF $C_2C_{12}$ membranes (200 µg) in PBS (250 µl) were incubated with 1, 5, 10, 50, 100, 500 or 1000 ng of either monoclonal antibody, chondroitin, dermatan or heparan sulfate and 20 nM (480 ng) of [$^{35}$S]PIF overnight at 4° C. The bound radioactivity was determined from the radioactivity in the pellet obtained by centrifugation at 13,000 g for 5 min.

The Kaff was determined according to a modification (Clark, B. R. and Todd, C. W. Avidin as a precipitant for biotin-labelled antibody in a radioimmunoassay for carcinoembryonic antigen. Anal. Biochem., 121: 257-262, 1982.) of the method of Muller (Muller, R.

Calculation of average antibody affinity in anti-hapten sera from data obtained by competitive radioimmunoassay. J. Immunol. Methods, 34: 345-352, 1980.).

$$Kaff = 1/(I_t - T_t)(1 - 1.56 + 0.5b^2)$$

where $I_t$ is the inhibitor concentration at 50% inhibition of PIF binding; $T_t$ the total PIF concentration; b the fraction of PIF bound in the absence of inhibitor.

Measurement of protein breakdown $C_2C_{12}$ myoblasts were labeled with L-[2,6-$^3$H]phenylalanine (0.5 µCi specific activity 0.72Ci mmol$^{-1}$) for 24 h. After labeling, cells were washed and incubated in fresh medium (3 ml) in the presence of PIF and cycloheximide (1 µm) for the required time, and the amount of radioactivity released into the medium was measured. Protein bound radioactivity was determined by washing the cells three-times with ice-cold PBS (1 ml, pH 7.4) and after removal of any residual PBS incubation was continued at 4° C. for 20 min with 0.2M perchloric acid (1 ml). The perchloric acid was removed and replaced with 1 ml of 0.3M NaOH at 4° C. for 30 min, followed by a further incubation at 37° C. for 20 min. The NaOH solution containing the dissolved cellular proteins was transferred to clean tubes and a further 1 ml of 0.3M NaOH was used to rinse the dishes. The rate of proteolysis was calculated by dividing the radioactivity released into the incubation medium by the protein-bound radioactivity.

1.2 Results

Binding studies have been conducted using [$^{35}$S]PIF, obtained by biosynthetically labeling MAC16 cells. The radioligand was purified from cell supernatants using a combination of affinity chromatography, followed by reverse phase hplc on a $C_8$ column. Ligand binding studies were performed using membranes isolated from the murine myoblast cell line $C_2C_{12}$ (results not shown) and the human muscle cell line Hs 94 MU (results not shown). In both species Scatchard analysis of the binding reaction provided evidence for two binding sites with Kd-$10^{-10}$ M and $10^{-9}$M (Table 1). Similar binding sites were observed in sarcolemma membranes isolated from the pig (results not shown). In sarcolemma membranes isolated from the gastrocnemius muscle of NMRI mice bearing the MAC16 (results not shown) and MAC13 tumors (results not shown), as well as liver plasma membranes (Table 1), two binding sites were also observed, with the $K_d$ of the lower affinity binding site being reduced from $10^{-9}$ to $10^{-10}$ M. There was no evidence for upregulation of receptor number in mice bearing the MAC16 tumor with cachexia in comparison with that found in sarcolemma membranes from mice bearing the MAC13 tumor, which does not induce cachexia. Plasma membranes from soleus muscle and heart also showed evidence for two binding sites for PIF (Table 1), while no receptor was detected on kidney or adipose tissue.

TABLE 1

Affinity constants for binding of PIF to plasma membranes

| Tissue Source | Kaff × $10^{-10}$M | Kaff$_2$ × $10^{-9}$M |
|---|---|---|
| $C_2C_{12}$ | 1.4 | 1.2 |
| Hs94MU | 1.1 | 1.7 |
| Pig | 4.7 | 8.2 |
| Mouse gastrocnemius muscle | 5.2 | 0.1 |
| Mouse liver | 6.9 | 0.2 |
| Mouse soleus muscle | 0.1 | 0.12 |
| Mouse heart | 3.0 | 2.3 |
| Mouse adipose | — nd | — nd | nd = non detectable

The biological activity of PIF is destroyed when the N- and O-linked oligosaccharide chains are removed by incubation with peptide: N-glycosidase F (PNGase F) or endo-α-N-acetylgalactosaminidase (O-glycosidase). To determine the effect of deglycosylation of PIF on binding to the receptor, experiments were conducted with peptide labeled PIF generated by incubating MAC16 cells with L-[2, 5$^{-3}$H] histidine. After 24 h incubation with PNGase F or O-glycosidase binding of [$^3$H] PIF was substantially reduced (FIG. 1), with only non-specific binding of the labeled polypeptide chain to the membrane.

The affinity of binding of PIF to monoclonal antibody (Kaff $10^8$M$^{-1}$) was found to be less than binding to either high or low affinity sites on the muscle receptor (results not shown). However, when the monoclonal antibody was added to $C_2C_{12}$ membranes at concentrations between 1 and 1000 ng/250 µl binding to the receptor was effectively inhibited (Kd $1.4\times10^{-8}$M). The monoclonal antibody was less effective at competing with membrane receptors for PIF, when added after PIF (Kd $5.8\times10^{-7}$M).

Although PIF is a sulfated glycoprotein the oligosaccharide chains have some similarity to a proteoglycan, since chondroitinase ABC destroys the antigenic determinants, and reduces the Mr, although no low molecular weight material corresponding to olisaccharides was obtained. This suggests that binding of PIF to the receptor may be attenuated by proteoglycans. To investigate this the effect of chondroitin, dermatan and heparan sulfate at concentrations between 5 and 5000 ng per assay on the binding of PIF to receptors on $C_2C_{12}$ membranes has been determined. Of the three proteoglycans only chondroitin sulfate showed competitive inhibition of binding (results not shown) with Kd $1.1\times10^{-7}$M.

Ligand blotting of [$^{35}$S]PIF to triton solubilized membranes from $C_2C_{12}$ cells electrophoresed in 15% SDS-PAGE and transferred electrophoretically to nitrocellulose filters provided evidence for a binding protein with apparent Mr 40,000 (FIG. 2A).

Increasing concentrations of non-labeled PIF were capable of displacing radioactivity from the binding proteins (FIG. 2B) confirming that binding to the receptor was specific.

Since $C_2C_{12}$ myoblasts possess receptors for PIF it was important to establish functional activity in this cell line. The effect of PIF on protein degradation was measured by the release of L-[2, 6-3H]phenylalanine in the presence of cycloheximide from cells pre-labeled for a 24 h period. An increased rate of protein degradation was observed within 6 h after the addition of PIF, which was maximal at concentrations between 0.98 and 1.4 nM (results not shown), which is close to the binding affinity of PIF to this cell line. Increased concentrations of PIF resulted in a decrease of phenylalanine release suggesting a negatively cooperative interaction between the two binding sites. Increased rates of protein degradation were observed over longer periods of time (24 and 48 h) at concentrations of PIF between 0.14 and 1.4 nM.

1.3 Discussion

In order for PIF to induce protein degradation in skeletal muscle there must be a specific interaction with a muscle protein receptor capable of translating the message into activation of the intracellular protein degradative system. Since PIF is a highly glycosylated and sulfated glycoprotein, it is likely that this will be membrane bound. The results of the present study provide evidence for specific, high affinity binding sites for PIF in muscle cells. The affinity of binding was comparable with that found for insulin and showed 10-100-fold greater affinity than binding to a monoclonal antibody, which has been utilised in the purification of PIF. However, high concentrations of the antibody were capable of displacing PIF from the membrane receptor. This would explain why high concentrations of the antibody were required to neutralise the biological effect of PIF. As with binding of PIF to the antibody, binding to the receptor is probably mediated through the sulfated oligosaccharide chains, since binding was specifically inhibited by chondroitin sulfate, but not by the related proteoglycans dermatan and heparan sulfate. In addition enzymatic deglycosylation resulted in the loss of specific binding of PIF to the receptor. The high affinity binding probably results from electrostatic interaction between PIF and the receptor.

A Scatchard plot of binding of PIF to muscle membranes from mouse, pig and man was nonlinear, indicating either two discrete sites, or cooperative interactions between the binding sites. Ligand blotting of [$^{35}$S] PIF to triton solubilized membranes from $C_2C_{12}$ cells electrophoresed in 15% SDS-PAGE, provided evidence for a binding protein of apparent Mr 40,000. Curvilinear Scatchard plots of steady state binding have been described for a number of hormonal and nonhormonal systems. For insulin this has been shown to represent negative cooperativity in the binding sites. This provides a mechanism in which binding to the receptor is favoured at low concentrations of the hormone, but becomes more difficult as the concentration of the hormone is increased. Such an effect is apparent for protein degradation in $C_2C_{12}$ cells induced by PIF, where a bell-shaped dose-response curve was observed. Previous studies have suggested similar dose-response curves for protein degradation in isolated soleus and gastrocnemius muscles induced by PIF. In addition the increased protein breakdown in tumor-bearing animals has been reported to decrease as the tumor size increases. These results suggest negative cooperative interactions between the PIF binding sites.

We have recently confirmed that PIF is responsible for the loss of skeletal muscle in mice bearing the MAC16 tumor with cachexia. However, the number of binding sites for PIF in skeletal muscle was comparable in mice bearing the MAC16 tumor and the MAC13 tumor, which does not induce cachexia, suggesting that the induction of muscle protein degradation during the process of cachexia is not due to upregulation of receptors. Instead it appears to be related to the production of PIF by the tumor, since urinary analysis showed PIF to be present only in cancer patients with weight loss, and not in those who were weight stable, or in non-cancer patients. Thus production of PIF by the tumor leads to constitutive activation of muscle protein degradation.

The distribution of the PIF receptor in tissues is commensurate with a role for PIF in mediating catabolism of skeletal muscle proteins. Protein degradation rates in $C_2C_{12}$ myoblasts were shown to increase by 50-90% in response to PIF, with maximal stimulation at a concentration of 0.98-1.4 nM, which is close to the binding affinity of PIF to the receptor. The role of PIF receptors in the liver is not known, since the liver responds to PIF by increasing in weight, rather than undergoing proteolysis as observed in skeletal muscle. This suggests that the PIF receptor in liver is not coupled to the second messenger system, which results in activation of proteolysis. The receptor may be used for removing PIF from the circulation or may result in activation of other systems, e.g. the acute phase response in hepatocytes.

Our studies to date have only identified PIF in association with cancer cachexia and not with other weight losing conditions. It is thus interesting to find muscle possessing a receptor for such a factor, even without prior exposure to PIF. The binding affinity and molecular weight of the receptor appear to be similar in mouse, pig and man suggesting a universality of function across the species. The natural agonist regulating skeletal muscle catabolism, e.g. during dietary deficiency or TNF-α-induced catabolic changes, is unknown, but may resemble PIF to the extent of cross-reactivity of receptors. Little is known about the intracellular processes controlling protein catabolism in skeletal muscle, but the end-result appears to be activation of the ATP-ubiquitin-dependent proteolytic system.

EXAMPLE 2

Having characterised PIF Binding sites (see Example 1), the inventors proceeded to isolate and sequence the PIF receptor according to the first aspect of the invention.
Isolation of the PIF Receptor from $C_2C_{12}$ Myotubes The inventors have established that Wheat Germ Agglutinin (WGA) (when linked to sephadex) will bind the oligosaccharide chains of PIF. This enabled them to effectively isolate the PIF receptor, after incubation with PIF, followed by lectin chromatography on WGA.

$C_2C_{12}$ membrane samples were prepared by sonicating in receptor buffer (20 mM HEPES pH 7.4, 1 mM EDTA, 0.5 mM PMSF, 1 mM DTT at 4° C.) and centrifuging at 20,000 rpm for 20 min. The pellet was washed and solubilized in 1% Triton for 30 min. The sample was then dialysed against PBS overnight at 4° C. 200 µl solubilized, dialysed sample was incubated with $^{35}$S PIF for 24 h at 4° C. in the presence of protease inhibitors, after which the PIF receptor was purified using a WGA column. The column (1 ml bed, 10 mg WGA/ml) was loaded with sample and washed with 20 volumes of wash buffer (10 mM Tris pH 7.4 with 0.02% $NaN_3$). Elution of the receptor was by 0.1M N-acetylglucosamine in wash buffer. 10 fractions (1 ml) were collected and stored at 4° C. in presence of protease inhibitors.

The radioactive fractions were concentrated using a Microcon centrifuge with a membrane to cut off proteins with a molecular mass less than 10 kDa, and were electrophoresed on 15% SDS-PAGE (FIG. 3). The receptor appeared as a single protein of apparent Mr 40 kDa. A similar molecular mass was evident from exclusion chromatography using Sephadex G-50 (results not shown). The PIF-receptor complex ran as a single fraction. A similar result was obtained after cross-linking of PIF to the receptor using glutaraldehyde (results not shown). Control incubations in which solubilized membranes isolated from $C_2C_{12}$ myotubes were subjected to lectin chromatography on WGA without prior incubation with PIF showed that no protein was eluted, confirming that the 40 kDa material was not an endogenous glycoprotein.
Sequence Analysis of PIF Receptor (Edman)
N-Terminus:

```
DINGGGATLPQPLYQTAAVLTAGFA       (SEQ ID No. 1)
```

This sequence matches a peptide fragment from a synovial fluid protein p205, with T-cell stimulatory activity (J. Immunol.; (1996) 157; 1773-80).

```
DINGGGATLPQKLYLIPNVL            (SEQ ID No. 13)
```

This further sequence is believed to represent a polymorphic variant receptor.
Internal Peptide Fragments

```
TAINDTFLNADSNLSIGK              (SEQ ID No. 2)

XATVAGVSPAPANVSAAIGA            (SEQ ID No. 3)

. . . IIPATTAGE . . .           (SEQ ID No. 4)

. . . TYMSPDYAAATLAG . . .      (SEQ ID No. 5)

FVPLPT                          (SEQ ID No. 6)

TELSNYVTAXGTxxG                 (SEQ ID No. 7)

VTTAGSDS                        (SEQ ID No. 8)

DVNGG                           (SEQ ID No. 9)

LTTWDLIADSGR                    (SEQ ID No. 10)
```

There is no sequence homology of the internal peptides with other proteins in the database.

EXAMPLE 3

Having sequenced the PIF receptor the inventors proceeded to develop agents for use according to the fourth, fifth or sixth aspects of the invention.

The inventors established that the peptide of SEQ ID No. 13 was able to block PIF binding to the PIF receptor and thereby demonstrated that the peptide may be used as an agent according to the fourth, fifth or sixth aspects of the invention.

3.1 Methods

The techniques employed in the purification of PIF and protein degradation assay, 'chymotrypsin-like' enzyme activity and Western blotting are described above and also contained in the following publications:
1. Gomes-Marcondes et al., Br. J. Cancer (2002) 86, 1628-1633.
2. Whitehouse and Tisdale, Br. J. Cancer (2003) 89, 1116-1122.
3. Smith and Tisdale, Br. J. Cancer (2003) 89, 1783-1788.

3.2 Results

PIF induced protein degradation in murine myotubes with a bell-shaped dose-response curve as previously reported (Gomes-Marcondes et al. supra) (FIG. 4). This effect was completely attenuated by the N-terminal synthetic peptide at a concentration of 10 μM. At this concentration the peptide also blocked the PIF-induced increase in chymotrypsin-like enzyme activity (FIG. 5), the predominant proteasome proteolytic activity.

Western blotting showed that the peptide also completely prevented the PIF-induced increase in expression of 20S proteasome α-subunits (FIG. 6A), two ATPase subunits of the 19S regulator of the proteasome MSS1 (FIG. 6B), p42 (FIG. 6C) as well as the ubiquitin-conjugating enzyme, $E2_{14k}$ (FIG. 6D). Inhibition of the induction of the ubiquitin-proteasome proteolytic pathway by the peptide resulted in attenuation of the PIF-induced decrease in expression of the myofibrillar protein myosin (FIG. 6E). These results suggest that PIF binds to the N-terminal region of the receptor peptide preventing interaction with the receptor in the myotubes.

These data clearly show that the peptide of SEQ ID No 1 may be used as an agent according to the present invention.

EXAMPLE 4

An antibody agent for use according to the fourth, fifth or sixth aspects of the invention was also investigated.

4.1 Methods

Polyclonal antiserum was generated to a 19-mer derived from the first 19 amino acids of the N-terminal peptide fragment (SEQ ID No. 13). The antiserum was produced in a rabbit under the terms of a confidential contract with Severn Biotech Ltd., Worcs, UK.

In more detail, polyclonal antiserum was produced by conjugating the 19mer peptide (5 mg) to 5 mg PPD (as carrier protein) with sulpho-SMCC through a C-terminal cysteine and subsequently immunising two rabbits by subcutaneous injection of the antigen (50-200 mg) at 0.25 ml at each of four sites in Freud's adjuvant. Serum was supplied from a test bleed, production bleed and terminal bleed.

The antiserum detected the PIF receptor by Western blotting (FIG. 7) after purification of the antibody by adding 50% saturated ammonium sulphate followed by Protein-A column chromatography (PURE1A kit, Sigma Aldridge, Dorset, UK).

Methods employed in Examples 1-3 were otherwise employed.

4.2 Results

The effect of the antibody to the PIF receptor at concentrations between 5 and 15 μg/ml on protein degradation induced by PIF is shown in FIG. 8. Partial attenuation of the PIF effect was seen at a concentration of 5 μg/ml, while complete attenuation was seen at concentrations of 10 μg/ml and higher. A similar effect was seen on the PIF-induced increase in chymotrypsin-like enzyme activity (FIG. 9).

Western blotting showed that in $C_2C_{12}$ myotubes, the anti-receptor antibody also completely prevented the PIF-induced increase in expression of 20S proteasome α-subunits (FIG. 10A), two ATPase subunits of the 19S regulator of the proteasome MSS1 (FIG. 10B), p42 (FIG. 10C) as well as the ubiquitin-conjugating enzyme, $E2_{14k}$ (FIG. 10D). These data clearly show that an antibody raised against the peptide of SEQ ID No 1 may be used as an agent according to the present invention.

To evaluate the ability of the anti-receptor antibody to prevent muscle protein degradation by PIF in vivo, mice bearing the cachexia-inducing MAC16 colon carcinoma, where PIF has been shown to be responsible for the loss of skeletal muscle (Lorite et al, Br. J. Cancer (1998) 78, 850-856), were treated daily by the i.p. administration of anti-PIF receptor polyclonal antisera (3.47 mg/kg). After 3 days treatment mice receiving the anti-receptor antibody had a significantly reduced weight loss compared with solvent controls (FIG. 11A). The effect on tumour volume is shown in FIG. 11B). There was a significant effect on protein synthesis (FIG. 12A) and a significant increase in the weight of the soleus muscle compared with solvent treated controls and this was not significantly different from weight matched NMRI mice without tumour (FIG. 12B). The anti-receptor antibody treatment attenuated protein degradation in soleus muscle down to that of non tumour-bearing mice (FIG. 12C), as well as functional proteasome activity, as measured by the chymotrypsin-like enzyme activity (FIG. 12D). Expression of 20S proteasome α-subunits (FIG. 13A), MSS1 (FIG. 13B), p42 (FIG. 13C) and $E2_{14k}$ (FIG. 13D) were all attenuated down to levels found in non tumour-bearing mice after treatment of cachectic mice with the anti-receptor antibody. The results in FIG. 13E show that the anti-receptor antibody reverses the loss of myosin in gastrocnemius muscle a seen in mice bearing the MAC16 tumour, up to levels found in non tumour-bearing mice. These data clearly show that an antibody raised against the peptide of SEQ ID No 1 may be used as an agent according to the present invention.

The invention claimed is:

1. An isolated antibody which specifically binds to the receptor for Proteolysis Inducing Factor (PIF) and blocks receptor-mediated intracellular signaling of the receptor, wherein the antibody specifically binds to peptide SEQ ID NO: 13.

2. The antibody of claim 1, wherein the antibody is polyclonal.

3. The antibody of claim 1, wherein the antibody is monoclonal.

4. The antibody of claim 1, wherein the antibody is a γ-immunoglobulin (IgG).

5. A method of decreasing the biological activity of the receptor for Proteolysis Inducing Factor (PIF), wherein the N terminus of the mature native receptor has an amino acid sequence of SEQ ID NO: 13, the method comprising binding the receptor with an agent which is an isolated antibody, or a fragment thereof, which specifically binds to the receptor and blocks receptor-mediated intracellular signaling of the receptor, wherein the agent is raised against peptide SEQ ID NO: 13.

6. The method of claim 5, wherein the agent is a polyclonal antibody.

7. The method of claim 5, wherein the agent is a monoclonal antibody.

8. The method of claim 5, wherein the agent is a γ-immunoglobulin (IgG) antibody.

9. The method of claim 5, wherein the agent is an antibody fragment.

10. The method of claim 9, wherein the agent is an scFV antibody.

11. The method of claim 5, wherein the agent is a humanized antibody.

12. A method for the treatment of cachexia comprising administering to a subject in need of such treatment a therapeutically effective amount of an agent that specifically binds to the receptor for Proteolysis Inducing Factor (PIF) and blocks receptor-mediated intracellular signaling of the receptor, wherein the N terminus of the mature native receptor has the amino acid sequence of SEQ ID NO: 13 and the agent is an antibody, or a fragment thereof, raised against peptide SEQ ID NO: 13.

13. The method of claim 12, wherein the agent is a polyclonal antibody.

14. The method of claim 12, wherein the agent is a monoclonal antibody.

15. The method of claim 12, wherein the agent is a γ-immunoglobulin (IgG) antibody.

16. The method of claim 12, wherein the agent is an antibody fragment.

17. The method of claim 16, wherein the antibody fragment is an scFV antibody.

18. The method of claim 12, wherein the agent is a humanized antibody.

* * * * *

UNITED STATES PATENT AND TRADEMARK OFFICE
CERTIFICATE OF CORRECTION

| | | |
|---|---|---|
| PATENT NO. | : 8,207,310 B2 | Page 1 of 1 |
| APPLICATION NO. | : 12/518881 | |
| DATED | : June 26, 2012 | |
| INVENTOR(S) | : Tisdale et al. | |

It is certified that error appears in the above-identified patent and that said Letters Patent is hereby corrected as shown below:

TITLE PAGE

(73) Delete "Ashton University, Birmingham (GB)"

and replace with --Aston University, Birmingham (GB)--

Signed and Sealed this
Sixteenth Day of October, 2012

David J. Kappos
*Director of the United States Patent and Trademark Office*

SEQUENCE LISTING

<160> NUMBER OF SEQ ID NOS: 15

<210> SEQ ID NO 1
<211> LENGTH: 25
<212> TYPE: PRT
<213> ORGANISM: Mus musculus

<400> SEQUENCE: 1

Asp Ile Asn Gly Gly Gly Ala Thr Leu Pro Gln Pro Leu Tyr Gln Thr
1               5                   10                  15

Ala Ala Val Leu Thr Ala Gly Phe Ala
            20                  25

```
<210> SEQ ID NO 2
<211> LENGTH: 18
<212> TYPE: PRT
<213> ORGANISM: Mus musculus

<400> SEQUENCE: 2

Thr Ala Ile Asn Asp Thr Phe Leu Asn Ala Asp Ser Asn Leu Ser Ile
1               5                   10                  15

Gly Lys

<210> SEQ ID NO 3
<211> LENGTH: 20
<212> TYPE: PRT
<213> ORGANISM: Mus musculus
<220> FEATURE:
<221> NAME/KEY: MISC_FEATURE
<222> LOCATION: (1)..(1)
<223> OTHER INFORMATION: Xaa is unknown

<400> SEQUENCE: 3

Xaa Ala Thr Val Ala Gly Val Ser Pro Ala Pro Ala Asn Val Ser Ala
1               5                   10                  15

Ala Ile Gly Ala
            20

<210> SEQ ID NO 4
<211> LENGTH: 9
<212> TYPE: PRT
<213> ORGANISM: Mus musculus

<400> SEQUENCE: 4

Ile Ile Pro Ala Thr Thr Ala Gly Glu
1               5

<210> SEQ ID NO 5
<211> LENGTH: 14
<212> TYPE: PRT
<213> ORGANISM: Mus musculus

<400> SEQUENCE: 5

Thr Tyr Met Ser Pro Asp Tyr Ala Ala Ala Thr Leu Ala Gly
1               5                   10

<210> SEQ ID NO 6
<211> LENGTH: 6
<212> TYPE: PRT
<213> ORGANISM: Mus musculus

<400> SEQUENCE: 6

Phe Val Pro Leu Pro Thr
1               5

<210> SEQ ID NO 7
<211> LENGTH: 15
<212> TYPE: PRT
<213> ORGANISM: Mus musculus
<220> FEATURE:
<221> NAME/KEY: MISC_FEATURE
<222> LOCATION: (10)..(10)
<223> OTHER INFORMATION: Xaa is unknown
<220> FEATURE:
<221> NAME/KEY: MISC_FEATURE
<222> LOCATION: (13)..(14)
<223> OTHER INFORMATION: Xaa is unknown
```

-continued

<400> SEQUENCE: 7

Thr Glu Leu Ser Asn Tyr Val Thr Ala Xaa Gly Thr Xaa Xaa Gly
1               5                   10                  15

<210> SEQ ID NO 8
<211> LENGTH: 8
<212> TYPE: PRT
<213> ORGANISM: Mus musculus

<400> SEQUENCE: 8

Val Thr Thr Ala Gly Ser Asp Ser
1               5

<210> SEQ ID NO 9
<211> LENGTH: 5
<212> TYPE: PRT
<213> ORGANISM: Mus musculus

<400> SEQUENCE: 9

Asp Val Asn Gly Gly
1               5

<210> SEQ ID NO 10
<211> LENGTH: 12
<212> TYPE: PRT
<213> ORGANISM: Mus musculus

<400> SEQUENCE: 10

Leu Thr Thr Trp Asp Leu Ile Ala Asp Ser Gly Arg
1               5                   10

<210> SEQ ID NO 11
<211> LENGTH: 75
<212> TYPE: DNA
<213> ORGANISM: Artificial sequence
<220> FEATURE:
<223> OTHER INFORMATION: Predicted sequence for the human N-terminal
      fragment SEQ ID NO: 1 based on the most common codon usage

<400> SEQUENCE: 11
gacatcaacg gcggcggcgc caccctgccc cagcccctgt accagaccgc cgccgtgctg      60
accgccggct tcgcc                                                      75

<210> SEQ ID NO 12
<211> LENGTH: 75
<212> TYPE: DNA
<213> ORGANISM: Artificial sequence
<220> FEATURE:
<223> OTHER INFORMATION: Synthetic sequence: Antisense molecule

<400> SEQUENCE: 12
ggcgaagccg gcggtcagca cggcggcggt ctggtacagg ggctggggca gggtggcgcc      60
gccgccgttg atgtc                                                      75

<210> SEQ ID NO 13
<211> LENGTH: 20
<212> TYPE: PRT
<213> ORGANISM: Mus musculus

<400> SEQUENCE: 13

Asp Ile Asn Gly Gly Gly Ala Thr Leu Pro Gln Lys Leu Tyr Leu Ile
1               5                   10                  15

Pro Asn Val Leu
            20

```
<210> SEQ ID NO 14
<211> LENGTH: 60
<212> TYPE: DNA
<213> ORGANISM: Artificial sequence
<220> FEATURE:
<223> OTHER INFORMATION: Predicted sequence for the human N-terminal
      fragment SEQ ID NO: 13 based on the most common codon usage

<400> SEQUENCE: 14
gacatcaacg gcggcggcgc caccctgccc cagaagctgt acctgatccc caacgtgctg      60

<210> SEQ ID NO 15
<211> LENGTH: 60
<212> TYPE: DNA
<213> ORGANISM: Artificial sequence
<220> FEATURE:
<223> OTHER INFORMATION: Synthetic sequence: Antisense molecule

<400> SEQUENCE: 15
cagcacgttg gggatcaggt acagcttctg gggcagggtg gcgccgccgc cgttgatgtc      60
```